United States Patent [19]

Grudzinskas et al.

[11] 4,228,296

[45] Oct. 14, 1980

[54] NOVEL 16-ARYLOXY-17,18,19,20-TETRANORPROSTANOIC ACIDS AND DERIVATIVES

[75] Inventors: Charles V. Grudzinskas, Garnerville, N.Y.; Martin J. Weiss, Oradell, N.J.

[73] Assignee: American Cyanamid Company, Stamford, Conn.

[21] Appl. No.: 6,164

[22] Filed: Jan. 24, 1979

Related U.S. Application Data

[62] Division of Ser. No. 520,064, Nov. 1, 1974.

[51] Int. Cl.$^2$ .................................. C07C 177/00
[52] U.S. Cl. ..................................... 560/60; 560/55; 560/61; 562/470
[58] Field of Search ..................... 560/55, 60, 61; 562/470

[56] References Cited

U.S. PATENT DOCUMENTS 3,931,279  1/1976  Nelson .................................. 560/53

FOREIGN PATENT DOCUMENTS 7206361  11/1972  Netherlands ............................. 560/53
7501560  8/1975  Netherlands ............................. 560/53

Primary Examiner—Paul J. Killos
Attorney, Agent, or Firm—Richard J. Hammond

[57] ABSTRACT

This disclosure describes novel 16-aryloxy-17,18, 19,20-tetranorprostanoic acids and derivatives thereof useful as bronchodilators and as hypotensive and contraceptive agents.

9 Claims, No Drawings

NOVEL 16-ARYLOXY-17,18,19,20-TETRANORPROSTANOIC ACIDS AND DERIVATIVES

This is a division of application Ser. No. 520,064 filed Nov. 1, 1974.

BRIEF SUMMARY OF THE INVENTION

This invention relates to novel 16-aryloxy-17,18,19,20-tetranorprostanoic acids, their derivatives and intermediates for preparing same. More specifically the novel compounds of this invention can be represented by the following two general formulae wherein A has the same absolute configuration as is found in the naturally-occurring mammallian prostaglandins, and all the racemates, racemic mixtures and diasteromeric mixtures thereof.

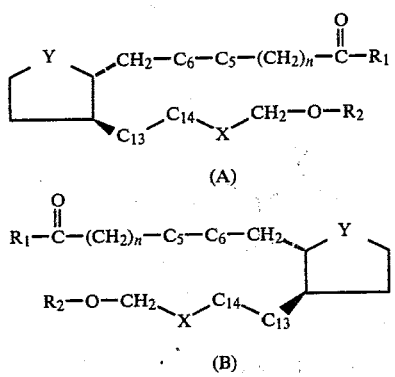

wherein $R_1$ is hydroxy or an alkoxy group having from one to twelve carbon atoms; $R_2$ is a phenyl, benzyl, naphthyl, or 5,6,7,8-tetrahydronaphthyl group optionally substituted with one or two of the following groups: halogen, lower alkyl, lower alkoxy, or trifluoromethyl radicals; n is an integer having the value 2 to 4, inclusive; Y is a divalent radical selected from the group consisting of

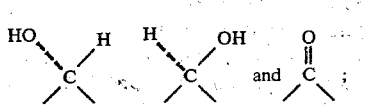

X is a divalent radical selected from the group consisting of

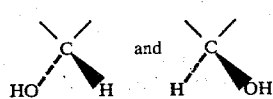

$C_5$–$C_6$ is ethylene or cis-vinylene; $C_{13}$–$C_{14}$ is ethylene or trans-vinylene; with the proviso that when $C_5$–$C_6$ is cis-vinylene then $C_{13}$–$C_{14}$ is trans-vinylene.

When X is

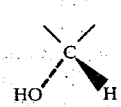

it represents the 15α-hydroxy derivative, and the 15β-hydroxy derivatives when it is

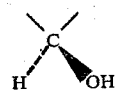

Suitable lower alkyl and lower alkoxy groups contemplated by the present invention are those having up to four carbon atoms such as, for example, methyl, propyl, iso-propyl, n-butyl, sec-butyl, methoxy, ethoxy, t-butoxy, etc.

Also embraced within the scope of the present invention are the non-toxic, pharmaceutically acceptable salts of the novel compounds of the present invention when $R_1$ is hydroxy. The cations comprised in these salts include, for example, the non-toxic metal cations such as the sodium ion, potassium ion, calcium ion, and magnesium ion as well as the organic amine cations such as the tri(lower alkyl)amine cations (e.g., triethylamine), procaine, and the like.

The novel compounds of the present invention are obtainable as yellow oils or crystalline solids having characteristics absorption spectra. They are relatively insoluble in water but are relatively soluble in common organic solvents such as ethanol, ethyl acetate, dimethylformamide, and the like. The cationic salts of the compounds when $R_1$ is hydroxy are, in general, white to yellow crystalline solids having characteristic absorption spectra. They are relatively soluble in water, methanol and ethanol but are relatively insoluble in benzene, diethyl ether, and petroleum ether.

DETAILED DESCRIPTION OF THE INVENTION

The prostaglandins are a family of closely related compounds which have been obtained from various animal tissues, and which stimulate smooth muscle, lower arterial blood pressure, antagonize epinephrine-induced mobilization of free fatty acids, and have other pharmacological and autopharmacological effects in mammals. See Bergstrom et al., *J. Biol. Chem.*, 238, 3555 (1963) and Horton, *Experienta*, 21, 113 (1965) and references cited therein. All of the so-called natural prostaglandins are derivatives of prostanoic acid.

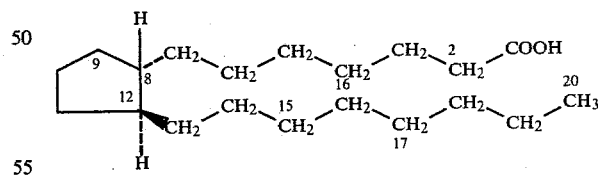

The hydrogen atoms attached to C-8 and C-12 are in trans configuration. The natural prostaglandins represent only one of the possible optical isomers. The compounds of this convention include all possible optical isomers.

The novel compounds of this invention are prepared from the corresponding known 11α-hydroxy-9-oxo-5-cis,13-trans-prostadienoic acids (I) (Netherlands Pat. No. 7,206,361; Nov. 14, 1972) as illustrated in Flowsheet A which follows and in which n, $R_2$ and $C_5$–$C_6$ are as hereinabove defined and in which THP is the tetrahydropyranyl group.

FLOWSHEET A

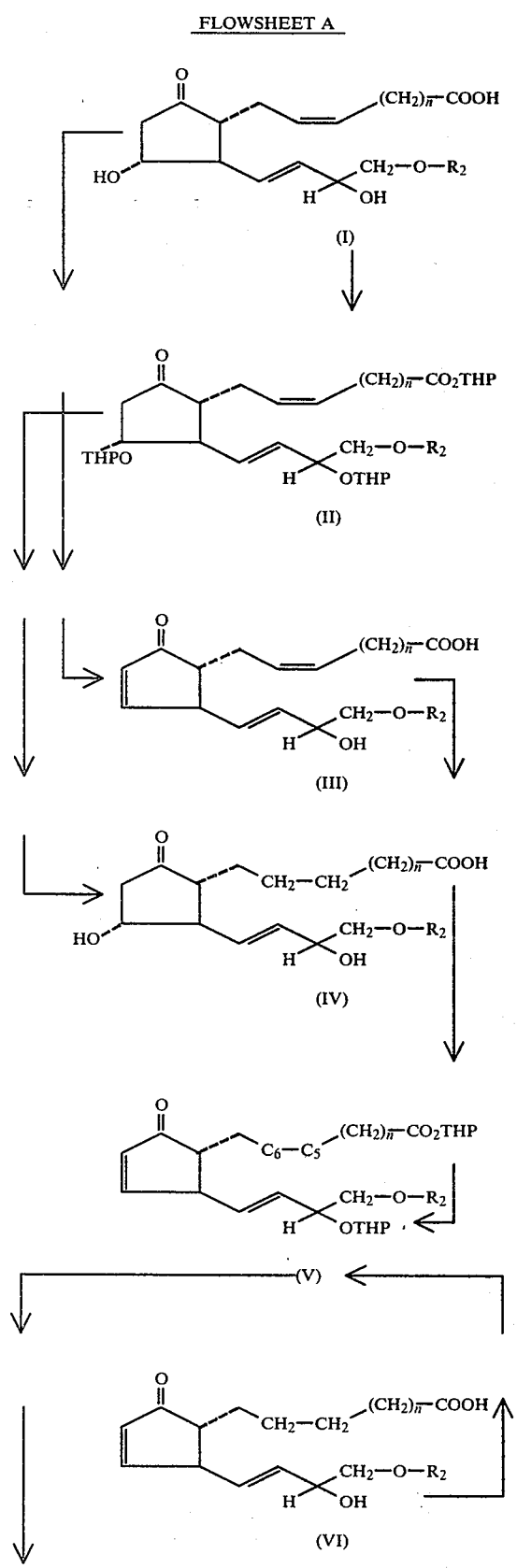

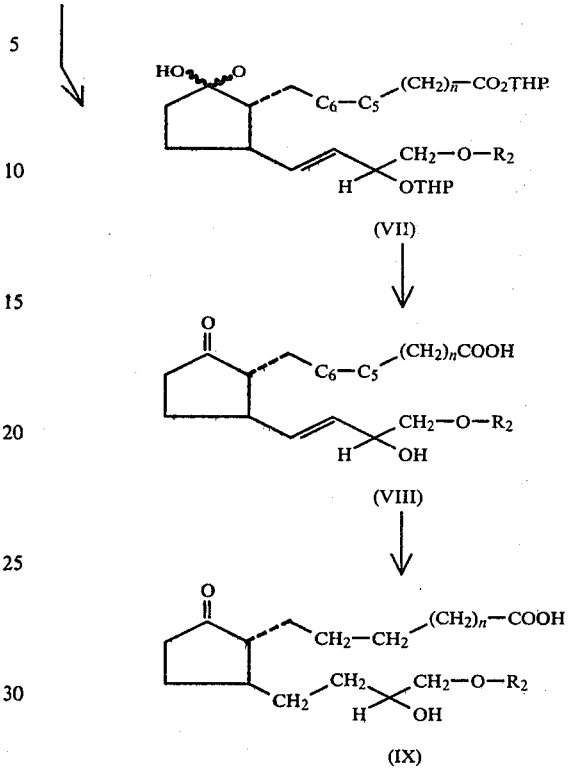

According to Flowsheet A above, dehydration of (I) in the usual manner provides the 16-aryloxy-15α-hydroxy-9-oxo-17,20-tetranor-5-cis,10,13-trans-prostatrienoic acids (III) which upon treatment with dihydropyran and acid provide the bistetrahydropyranyl derivative (V). Upon treatment of (V) with sodium borohydride or sodium cyanoborohydride (pH3–4), a mixture (VII) of 9α,15α-dihydroxy-16-aryloxy-9-oxo-17,20-tetranor-5-cis,13-trans-prostadienoic acid and the corresponding 9α-hydroxyl prostadienoic acid is obtained. Oxidation of the 9-hydroxy mixture (VII) provides, after acidic hydrolysis of the tetrahydropyranyl functions, the 16-aryloxy-15α-hydroxy-9-oxo-17,20-tetranor-5-cis,13-trans-prostadienoic acid (VIII), which upon hydrogenation provides the fully saturated 16-aryloxy-15α-hydroxy-9-oxo-17,20-tetranorprostanoic acids (IX).

Treatment of the 16-aryloxy-11α,15α-dihydroxy-17,20-tetranor-5-cis,13-trans-prostadienoic acids (I) with dihydropyran and an acid catalyst provides the tris-tetrahydropyranyl derivatives (II) which can be selectively reduced at the $C_5$–$C_6$ cis double bond. Acid-catalyzed hydrolysis of the tetrahydropyranyl moieties then provides the 11α,15α-dihydroxy-9-oxo-16-aryloxy-17,20-tetranor-13-trans-prostenoic acids (IV), which when subjected to the steps as described above for I→III→V→VII→VIII provides the 15α-hydroxy-9-oxo-16-aryloxy-17,20-tetranor-13-trans-prostenoic acids of this invention.

The 9-hydroxy derivative of this invention can also be obtained by reduction of the corresponding 9-oxo derivative. When the reduction is carried out in the usual manner with sodium borohydride in ethanol as solvent, the product is a mixture of the 9α- and 9β- hydroxy derivative (X) and (XI), respectively. These isomers are separable by chromatographic procedures. The stereoselective preparation of the 9α-hydroxy derivative (X) can be accomplished by reduction of the 9-oxo derivative with either lithium perhydro-9b-boraphenalyl hydride [H. C. Brown and W. C. Dickason, *Jour. Amer. Chem. Soc.*, 92, 709 (1970)] or with lithium tri-sec-butylborohydride.

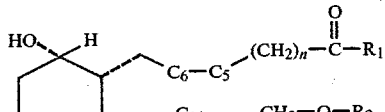

(X)

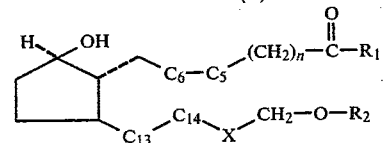

(XI)

The carboxylic acid esters ($R_1$=alkoxy) of this invention can be prepared by treating the corresponding carboxylic acid with the appropriate diazoalkane by the usual procedures well known to the art. An alternative procedure involves blocking the 15-hydroxy function with a tetrahydropyranyl group, conversion of the carboxylic acid to an acid chloride and reacting with the appropriate alcohol in the presence of an acid-acceptor and deblocking.

All of the compounds of this invention can be isolated and purified by conventional methods. Isolation can be accomplished, for example, by dilution of the reaction mixture with water, extraction with a water-immiscible solvent such as methylene chloride, ethyl acetate, benzene, cyclohexane, ether, toluene and the like, chromatography, adsorption on ion-exchange resins, distillation, or a combination of these. Purification of the compounds of this invention can be accomplished by means known in the art for the purification of prostaglandins and lipids, fatty acids, and fatty esters. For example, partition chromatography, reverse phase partition chromatography, countercurrent distribution, adsorption chromatography on acid washed Florisil ® (synthetic magnesium silicate) and acid washed silica gel, dry column chromatography, preparative paper chromatography, preparative thin layer chromatography, chromatography over sili-ca loaded cation exchange resins, and combinations thereof can be used effectively to purify the compounds produced by the presence of this invention.

If a compound of this invention is prepared from a prostaglandin A (III, V, VI) which is in the optically active resolved from, then the product will also be in the resolved form. On the other hand, if the prostaglandin A is racemic, the product will be racemic.

In formulae XII-XXIII, which follow, $R_2$, n, X, $C_5$-$C_6$ and $C_{13}$-$C_{14}$ are as hereinabove defined.

The racemic products and intermediates of this invention may be resolved into their optically active components by a number of methods of resolution well known in the art. For example, the free carboxylic acids can be treated with an optically active base such as cinchonine, quinine, brucine, d- or l-α-phenylethylamine and the like to produce diastereoisomeric salts which can be separated by crystallization. Alternatively, the acid may be esterified with an optically active alcohol, e.g., di- or l-menthol, estradiol 3-acetate, etc., and the diastereoisomeric esters then resolved.

Resolution of the racemic prostaglandin-like compounds of this invention may also be accomplished by reverse phase and absorption chromatography on an optically active support and adsorbent and by selective transformation of one isomer with a biologically-active prostaglandin, transforming system. Such transformations can be carried out by incubation or perfusion, using methods well established in the art, followed by isolation and recovery of the isomer resistant to the metabolic transformation applied.

Additional procedures for effecting the resolution of the racemic products of this invention involve conversion of a 9α-hydroxy racemate (illustrated by XII and XIII below) to the corresponding hemiphthalate (e.g., XIV) and conversion of this diacid to a bis salt (e.g., XV) with an optically active amine (e.g., 1-(−)-α-methylbenzylamine, d-(+)-α-methylbenzylamine, brucine, dehydroabietylamine, strychnine, quinine, cinchonine, cinchonidine, quinidine, ephedrine, deoxyephedrine, amphetamine, (+)-2-amino-1-butanol (−)-2-amino-1-butanol and the like). The resulting diastereoisomers are then separated by fractional crystallization and the individual components are then converted by acidification and saponification to the individual optically active parent 9α-hydroxy enantiomers (XII) and (XIII), oxidation of which provides the corresponding individual 9-oxo enantiomers (XVI) and (XVII).

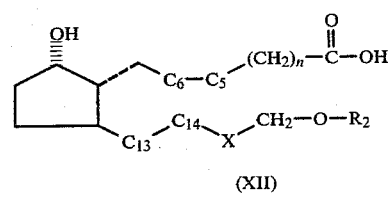

(XII)

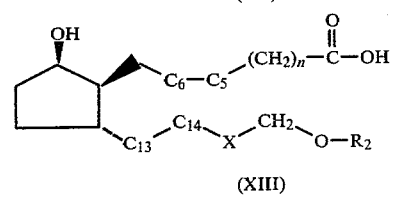

(XIII)

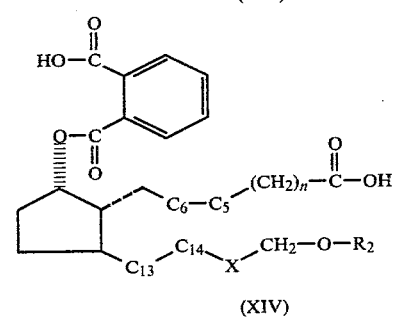

(XIV)

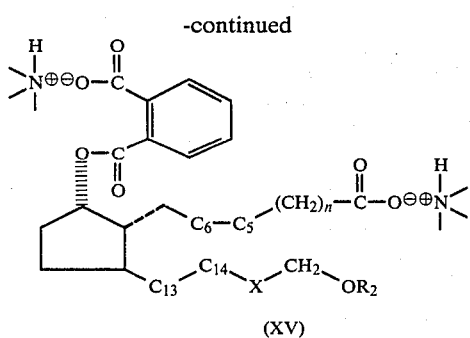

(XV)

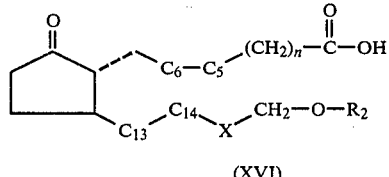

(XVI)

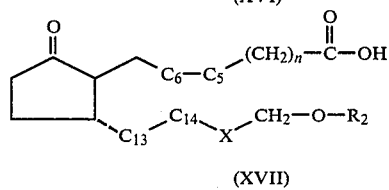

(XVII)

Another procedure involves conversion of the 9α-hydroxy racemate (as the 15-hydroxy blocked and then deblocked prostenoic acid ester) to the diastereomeric carbamates with an optically active isocyanate, e.g., (+)-1-phenylethylisocyanate and (−)-1-phenylethylisocyanate. Separation of the diastereomers, for example, (XVIII) and (XIX), can be accomplished by fractional crystallization or by the usual chromatographic procedures, or if necessary by high speed liquid chromatography involving, if required, recycling techniques [See G. Fallick, *American Laboratory*, 19–27 (August, 1973) as well as references cited therein. Additional information concerning high speed liquid chromatography and the instruments necessary for its application is available from Waters Associates Inc., Maple St., Milford, Mass.] Base-treatment of the individual diastereomeric carbamates then affords the individual enantiomeric alcohols.

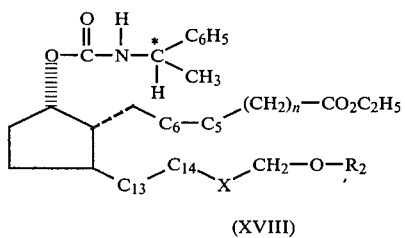

(XVIII)

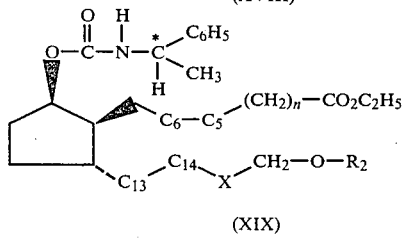

(XIX)

It is also possible to effect resolution of the 9α-hydroxy racemate, preferably as the prostenoate ester, by esterification of the 9α-hydroxy function (15-hydroxy function blocked as a tetrahydropyranyl ether or trimethylsilyl ester and then deblocked after 9α-hydroxyfunctionally action) with an optically active acid, via its acid chloride. Suitable optically active acids include ω-camphoric acid, menthoxyacetic acid, 3β-acetoxy-Δ⁵-etianic acid, (−)-α-methoxy-α-trifluoromethylphenyl acetic acid and (+)-α-methoxy-α-trifluoromethylphenylacetic acid, and the like. The resulting diastereoisomeric esters, for example (XX) and (XXI) are then separated by fractional crystallization or by chromatographic techniques including if necessary, the use of high speed liquid chromatography. Saponification of the individual diastereoisomers then provides the individual 9α-hydroxyprostenoic acid enantiomers (XII) and (XIII).

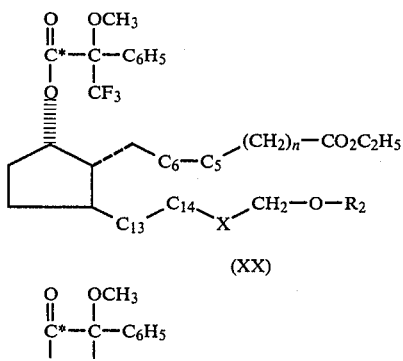

(XX)

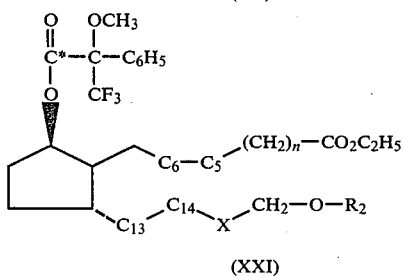

(XXI)

Another resolution procedure involves derivatization of the keto function of the racemic 9-oxoprostenoic acid or ester with the usual type of ketone derivatizing agents bearing an optically active center. The resulting mixture of diastereomeric derivatives can then be separated by fractional crystallization or by chromatography or, if necessary, by high speed liquid chromatography. The individual diastereomeric keto derivatives, for example, (XXII) and (XXIII), are then convertable to the individual 9-oxo enantiomers (XVI) and (XVII) by any of the usual cleavage techniques. Ketone reduction of the 9-oxo-enantiomer as described hereinabove then provides the corresponding 9α-hydroxy or 9β-hydroxy enantiomer. Among the optically active reagents useful for ketone derivatization are 1-α-aminoxy-γ-methylpentanoic acid hydrochloride [E. Testa et al., *Helv. Chimica Acta*, 47 (3), 766 (1973)], menthylhydrazine, and 4-α-methylbenzylsemicarbazide.

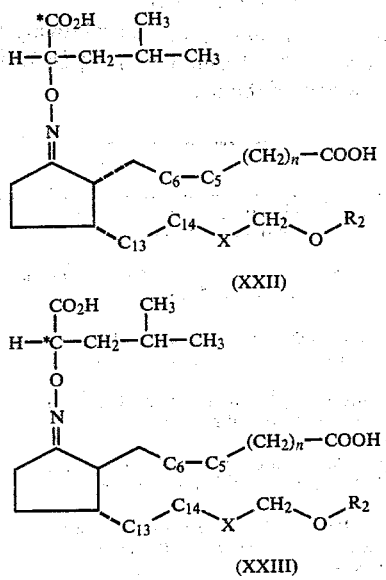

Other useful keto derivating agents are optically active 1,2-glycols, e.g., D(—)-2,3-butanediol, [for pertinent literature see, A. C. Neish, Can. Jour. Res. 23 sec. B, 10 (1945); G. E. Ward et al., Jour. Amer. Chem. Soc., 66, 541 (1944); J. Casanova, Jr. and E. J. Corey, Chem. and Ind. (London), 1961, 1964)] or optically active dithiols, e.g., L(+)-2,3-butanedithiol [see also E. J. Corey and R. B. Miha, Jour. Amer. Chem. Soc., 84, 2938 (1962)].

The novel compounds of this invention are useful as hypotensive agents (9-oxo derivatives), bronchodilators for the treatment of asthma and as agents for the control of reproduction in females, in humans as well as in warm-blooded animals such as cattle, sheep, swine, horses, dogs and cats. Among the potential uses in domestic animals is the synchronization of oestrus in cattle and other domestic animals, and the induction of twinning.

In humans these compounds may have use as agents for the induction of labor at term, as abortifacients and as menses inducers.

There are several possibilities of contraceptive attack during the normal processes of mammalian female reproduction. These include any others ovulation blockage, interference with the fertilization of the ovum by sperm, interference with the normal transport of ova and or zygotes in the reproductive tract, prevention of embryo implantation, disruption of the maternal response to embryonic implantation, and maternal failure to support embryonic survival. While the exact mechanism or mechanisms which take place with the active ingredients in effecting contraception is not clear, the compounds of this invention may prevent conception by one or more of the above-mentioned occurrences. It is not intended, however, that the present invention be limited to any particular theory as to mechanism of contraception.

A major problem in the clinical use of prostaglandin $E_2$ and prostaglandin $F_2\alpha$, and indeed of prostaglandins of the 11α-hydroxy series in general, is the often high incidence of gastrointestinal side-effects as manifested by nausea, vomiting and diarrhea. Presumably, these effects result from the stimulation of gastrointestinal smooth muscle by the administered prostaglandin. One important advantage of the compounds of this invention is that although they retain to a significant extent the antifertility potency of the parent 11-hydroxy compounds they show a highly diminished ability to stimulate smooth myscle. This very significant and unanticipated separation of biological effects suggests that the compounds of this invention have the potential to be useful anti-fertility agents with a minimum of adverse side-effects. It is also conceivable that this separation will allow the use of higher relative doses of these compounds than hitherto possible with the established prostaglandins. This also denotes the possibilities of more effective application in the field of post-conception control, e.g. inducing menses during approximately the first two weeks following the first missed menstruation. For a discussion of these problems see Toppozada et al. "Prostaglandins in Fertility Control" 3, 108 (1973), Report from Meetings of the Prostaglandin Task Force Steering Committee sponsored by the World Health Organization; and Wiqvist et al., ibid. 3, 83 (1973).

The invention will be described in greater detail in conjunction with the following specific examples.

EXAMPLE 1

Preparation of d,l-11α,15α-dihydroxy-9-oxo-16-phenoxy-17,20-tetranor-5-cis-13-trans-prostadienoic acid A mixture of the 15 epimers of dl-16-phenoxy-9α,1α,15-trihydroxy-17,20-tetranor-5-cis-13-trans-prostadienoic acid is prepared in accordance with Netherlands Pat. No. 7,206,361, page 9, Example 1. The two epimers are separated by the procedure of Netherlands Pat. No. 7,206,361, page 9, Example 1. The high Rf material is assigned the 15β configuration and the low Rf material is assigned the 15α-configuration. dl-16-Phenoxy-9α,11α,15-trihydroxy-17,20-tetranor-5-cis-13-trans-prostadienoic acid (100 mg.) is dissolved in 2.0 ml. of dry acetone and stirred at —40° C. under argon, N-trimethylsilyldimethylamine (3 ml.) is then added and after 1 hour the reaction is diluted with cold ether and extracted with 50% saturated aqueous sodium bicarbonate. Evaporation to dryness in vacuo yields as the major product: dl-11α,15α-bistrimethylsiloxy-9α-hydroxy-16-phenoxy-17,20-tetranor-5-cis-13-trans-prostadienoic acid trimethylsilyl ester.

The crude material is oxidized with Collins reagent (prepared in situ from 170 mg. of chromic anhydride and 275 ml. of pyridine in 4 ml. of methylene chloride) for 5 minutes at 25° C. The reaction mixture is diluted with ether and extracted with 0.5 M hydrochloric acid washed with brine. The organic solution is dried with magnesium sulfate and concentrated in vacuo to give the crude dl-11α,15-bistrimethylsiloxy-9-oxo-16-phenoxy-17,20-tetranor-5-cis-13-trans-prostadienoic acid trimethylsilyl ester.

The crude trimethylsilyl ester is dissolved in 5 ml. of methanol containing 0.5 ml. of water and 0.25 ml. of acetic acid and stirred at ambient temperature for 1 hour. The solution is diluted with 5 ml. of 30% aqueous potassium hydrogen phosphate and extracted twice with 10 ml. of ether. The ether is dried with magnesium sulfate and concentrated in vacuo to afford dl-11α,15α-dihydroxy-9-oxo-16-phenoxy-17,20-tetranor-5-cis-13-trans-prostatrienoic acid as an oil.

The crude oil is purified by dry column chromatography on silica gel to give dl-11α,15α-dihydroxy-9-oxo- 16-phenoxy-17,20-tetranor-5-cis-13-trans-prostatrienoic acid.

EXAMPLES 2-57

Treatment of the compounds of the following table by the procedure of Example 1 is productive of the 9-oxo derivatives of the table.

| Example | Starting Compound | 9-Oxo Product |
|---|---|---|
| 2 | dl-9α,11α,15α-trihydroxy-16-benzyloxy-17,20-tetranor-5-cis,13-trans-prostadienoic acid | dl-11α,15α-dihydroxy-9-oxo-16-benzyloxy-17,20-tetranor-5-cis,13-trans-prostadienoic acid |
| 3 | dl-9α,11α,15α-trihydroxy-16-(2-naphyloxy)-17,20-tetranor-5-cis,13-trans-prostadienoic acid | dl-11α,15α-dihydroxy-9-oxo-16-(2-naphthyloxy)-17,20-tetranor-5-cis,13-trans-prostadienoic acid |
| 4 | dl-9α,11α,15α-trihydroxy-16-p-chlorophenoxy-17,20-tetranor-5-cis,13-trans-prostadienoic acid | dl-11α,15α-dihydroxy-9-oxo-16-p-chlorophenoxy-17,20-tetranor-5-cis,13-trans-prostadienoic acid |
| 5 | dl-9α,11α,15α-trihydroxy-16-m-chlorophenoxy-17,20-tetranor-5-cis,13-trans-prostadienoic acid | dl-11α,15α-dihydroxy-9-oxo-16-m-chlorophenoxy-17,20-tetranor-5-cis,13-trans-prostadienoic acid |
| 6 | dl-9α,11α,15α-trihydroxy-16-o-chlorophenoxy-17,20-tetranor-5-cis,13-trans-prostadienoic acid | dl-11α,15α-dihydroxy-9-oxo-16-o-chlorophenoxy-17,20-tetranor-5-cis,13-trans-prostadienoic acid |
| 7 | dl-9α,11α,15α-trihydroxy-16-(2,4-dichlorophenoxy)-17,20-tetranor-5-cis,13-trans-prostadienoic acid | dl-11α,15α-dihydroxy-9-oxo-16-(2,4-dichlorophenoxy)-17,20-tetranor-5-cis,13-trans-prostadienoic acid |
| 8 | dl-9α,11α,15α-trihydroxy-16-p-bromophenoxy-17,20-tetranor-5-cis,13-trans-prostadienoic acid | dl-11α,15α-dihydroxy-9-oxo-16-p-bromophenoxy-17,20-tetranor-5-cis,13-trans-prostadienoic acid |
| 9 | dl-9α,11α,15α-trihydroxy-16-p-fluorophenoxy-17,20-tetranor-5-cis,13-trans-prostadienoic acid | dl-11α,15α-dihydroxy-9-oxo-16-p-fluorophenoxy-17,20-tetranor-5-cis,13-trans-prostadienoic acid |
| 10 | dl-9α,11α,15α1β-trihydroxy-16-p-methylphenoxy-17,20-tetranor-5-cis,13-trans-prostadienoic acid | dl-11α,15α/β-dihydroxy-9-oxo-16-p-methylphenoxy-17,20-tetranor-5-cis,13-trans-prostadienoic acid |
| 11 | dl-9α,11α,15α-trihydroxy-16-m-methylphenoxy-17,20-tetranor-5-cis,13-trans-prostadienoic acid | dl-11α,15α-dihydroxy-9-oxo-16-m-methylphenoxy-17,20-tetranor-5-cis,13-trans-prostadienoic acid |
| 12 | dl-9α,11α,15α/β-trihydroxy-16-p-t-butylphenoxy-17,20-tetranor-5-cis,13-trans-prostadienoic acid | dl-11α,15α/β-dihydroxy-9-oxo-16-p-t-butylphenoxy-17,20-tetranor-5-cis,13-trans-prostadienoic acid |
| 13 | dl-9α,11α,15α-trihydroxy-16-p-trifluoromethylphenoxy-17,20-tetranor-5-cis,13-trans-prostadienoic acid | dl-11α,15α-dihydroxy-9-oxo-16-p-trifluoromethylphenoxy-17,20-tetranor-5-cis,13-trans-prostadienoic acid |
| 14 | dl-9α,11α,15α-trihydroxy-16-p-methoxyphenoxy-17,20-tetranor-5-cis,13-trans-prostadienoic acid | dl-11α,15α-dihydroxy-9-oxo-16-p-methoxyphenoxy-17,20-tetranor-5-cis,13-trans-prostadienoic acid |
| 15 | dl-9α,11α,15α-trihydroxy-16-o-methoxy-17,20-tetranor-5-cis,13-trans-prostadienoic acid | dl-11α,15α-dihydroxy-9-oxo-16-o-methoxyphenoxy-17,20-tetranor-5-cis,13-trans-prostadienoic acid |
| 16 | dl-9α,11α,15α-trihydroxy-16-m-fluorophenoxy-17,20-tetranor-5-cis,13-trans-prostadienoic acid | dl-11α,15α-dihydroxy-9-oxo-16-m-fluorophenoxy-17,20-tetranor-5-cis,13-trans-prostadienoic acid |
| 17 | dl-9α,11α,15α-trihydroxy-16-o-fluorophenoxy-17,20-tetranor-5-cis,13-trans-prostadienoic acid | dl-11α,15α-dihydroxy-9-oxo-16-o-fluorophenoxy-17,20-tetranor-5-cis,13-trans-prostadienoic acid |
| 18 | dl-9α, 11α,15α-trihydroxy-16-(3,4-dichlorophenoxy)-17,20-tetranor-5-cis,13-trans-prostadienoic acid | dl-11α,15α-dihydroxy-9-oxo-16-(3,4-dichlorophenoxy)-17,20-tetranor-5-cis,13-trans-prostadienoic acid |
| 19 | dl-9α,11α,15α-trihydroxy-16-(2,5-dichlorophenoxy)-17,20-tetranor-5-cis,13-trans-prostadienoic acid | dl-11α,15α-dihydroxy-9-oxo-16-(2,5-dichlorophenoxy)-17,20-tetranor-5-cis,13-trans-prostadienoic acid |
| 20 | dl-9α,11α,15α-trihydroxy-16-o-methylphenoxy-17,20-tetranor-5-cis,13-trans-prostadienoic acid | dl-11α,15α-dihydroxy-9-oxo-16-o-methylphenoxy-17,20-tetranor-5-cis,13-trans-prostadienoic acid |
| 21 | dl-9α,11α,15α-trihydroxy-16-(2.3-dimethylphenoxy)-17,20-tetranor-5-cis, 13-trans-prostadienoic acid | dl-11α,15α-dihydroxy-9-oxo-16(2,3-dimethylphenoxy)-17,20-tetranor-5-cis,13-trans-prostadienoic acid |
| 22 | dl-9α,11α,15α-trihydroxy-16-(3,5-dimethylphenoxy)-17,20-tetranor-5-cis,13-trans-prostadienoic acid | dl-11α,15α-dihydroxy-9-oxo-16-(3,5-dimethylphenoxy)-17,20-tetranor-5-cis,13-trans-prostadienoic acid |
| 23 | dl-9α,11α,15α-trihydroxy-16-(2-chloro-4-methylphenoxy)-17,20-tetranor-5 cis,13-trans-prostadienoic acid | dl-11α,15α-dihydroxy-9-oxo-16-(2-chloro-4-methylphenoxy)-17,20-tetranor-5-cis,13-trans-prostadienoic acid |
| 24 | dl-9α,11α,15α-trihydroxy-16-m-dimethylaminophenoxy-17,20-tetranor-5-cis, 13-trans-prostadienoic acid | dl-11α,15α-dihydroxy-9-oxo-16-m-dimethylaminophenoxy,17,20-tetranor-5-cis,13-trans-prostadienoic acid |
| 25 | dl-9α,11α,15α-trihydroxy-16-(1-naphthyloxy)-17,20-tetranor-5- | dl-11α,15α-dihydroxy-9-oxo-16-(1-naphthyloxy)-17,20-tetranor-5-cis,13-trans-prostadienoic |

-continued

| Example | Starting Compound | 9-Oxo Product |
|---|---|---|
| | cis,13-trans-prostadienoic acid | acid |
| 26 | dl-9α,11α,15α-trihydroxy-16-(4-chloro-1-naphthyloxy)-17,20-tetranor-5-cis,13-trans-prostadienoic acid | dl-11α,15α-dihydroxy-9-oxo-16-(4-chloro-1-naphthyloxy)-17,20-tetranor-5-cis,13-trans-prostadienoic acid |
| 27 | dl-9α,11α,15α-trihydroxy-16-(6-methyl-2-naphthyloxy)-17,20-tetranor-5-cis,13-trans-prostadienoic acid | dl-11α,15α-dihydroxy-9-oxo-16-(6-methyl-2-naphthyloxy)-17,20-tetranor-5-cis,13-trans-prostadienoic acid |
| 28 | dl-9α,11α,15α-trihydroxy-16-(6-methoxy-2-naphthyloxy)-17,20-tetranor-5-cis,13-trans-prostadienoic | dl-11α,15α-dihydroxy-9-oxo-16-(6-methoxy-2-naphthyloxy)-17,20-tetranor-5-cis,13-trans-prostadienoic acid |
| 29 | dl-9α,11α,15-trihydroxy-16-(2,3-dichloro)-17,20-tetranor-5-cis-13 trans-prostadienoic acid | dl-11α,15α-dihydroxy-9-oxo-16-(2,3-dichlorophenoxy)-17,20-tetranor-5-cis,13-trans-prostadienoic acid |
| 30 | dl-9α,11α,15α-trihydroxy-16-(2,6-dichlorophenoxy)-17,20-tetranor-5-cis 13-trans-prostadienoic acid | dl-11α,15α-dihydroxy-9-oxo-16-(2,6-dichlorophenoxy)-17,20-tetranor-5-cis,13-trans-prostadienoic acid |
| 31 | dl-9α,11α,15α-trihydroxy-16-(3,5-dichlorophenoxy)-17,20-tetranor-5-cis,13-trans-prostadienoic acid | dl-11α,15α-dihydroxy-9-oxo-16-(3,5-dichlorophenoxy)-17,20-tetranor-5-cis,13-trans-prostadienoid acid |
| 32 | dl-9α,11α,15α-trihydroxy-16-(4-chloro-3-methylphenoxy)-17,20-tetranor-5-cis,13-trans-prostadienoic acid | dl-11α,15α-dihydroxy-9-oxo-16-(4-chloro-3-methylphenoxy)-17,20-tetranor-5-cis,13-trans-prostadienoic acid |
| 33 | dl-9α,11α,15α-trihydroxy-16-m-methoxyphenoxy-17,20-tetranor-5-cis,13-trans-prostadienoic acid | dl-11α,15α-dihydroxy-9-oxo-16-m-methoxyphenoxy-17,20-tetranor-5-cis,13-trans-prostadienoic acid |
| 34 | dl-9α,11α,15α/β-trihydroxy-16-(1-chloro-2-naphthyloxy)-17,20-tetranor-5-cis,13-trans-prostadienoic | dl-11α,15α/β-dihydroxy-9-oxo-16-(1-chloro-2-naphthyloxy)-17,20-tetranor-5-cis, 13-trans-prostadienoic acid |
| 35 | dl-9α,11α,15α-trihydroxy-16-(5,6,7,8-tetrahydro-2-naphthyloxy)-17,20-tetranor-5-cis,13-trans-prostadienoic acid | dl-11α,15α-dihydroxy-9-oxo-16-(5,6,7,8-tetrahydro-2-naphthyloxy)-17,20-tetranor-5-cis,13-trans-prostadienoic acid |
| 36 | dl-9α,11α,15β-trihydroxy-16-benzyloxy-17,20-tetranor-5-cis,13-trans-prostadienoic acid | dl-11α,15β-dihydroxy-9-oxo-16-benzyloxy-17,20-tetranor-5-cis,13-trans-prostadienoic acid |
| 37 | dl-9α,11α,15β-trihydroxy-16-(2-naphthyloxy)-17,20-tetranor-5-cis,13-trans-prostadienoic acid | dl-11α,15β-dihydroxy-9-oxo-16-(2-naphthyloxy)-17,20-tetranor-5-cis,13-trans-prostadienoic acid |
| 38 | dl-9α,11α,15β-trihydroxy-16-p-chlorophenoxy-17,20-tetranor-5-cis,13-trans-prostadienoic acid | dl-11α,15β,15β-dihydroxy-9-oxo-16-p-chlorophenoxy-17,20-tetranor-5-cis,13-trans-prostadienoic acid |
| 39 | dl-9α,11α,15β-trihydroxy-16-m-chlorophenoxy-17,20-tetranor-5-cis,13-trans-prostadienoic acid | dl-11α,15β-dihydroxy-9-oxo-16-m-chlorophenoxy-17,20-tetranor-5-cis,13-trans-prostadienoic acid |
| 40 | dl-9α,11α,15β-trihydroxy-16-o-chlorophenoxy-17,20-tetranor-5-cis,13-trans-prostadienoic acid | dl-11α,15β-dihydroxy-9-oxo-16-o-chlorophenoxy-17,20-tetranor-5-cis,13-trans-prostadienoic acid |
| 41 | dl-9α,11α,15β-trihydroxy-16-(2,4-dichlorophenoxy)-17,20-tetranor-5-cis,13-trans-prostadienoic acid | dl-11α,15β-dihydroxy-9-oxo-16-(2,4-dichlorophenoxy-17,20-tetranor-5-cis,13-trans-prostadienoic acid |
| 42 | dl-9α,11α,15β-trihydroxy-16-p-fluorophenoxy-17,20-tetranor-5-cis,13-trans-prostadienoic acid | dl-11α,15β-dihydroxy-9-oxo-16-p-fluorophenoxy-17,20-tetranor-5-cis,13-trans-prostadienoic acid |
| 43 | dl-9α,11α,15β-trihydroxy-16-m-methylphenoxy-17,20-tetranor-5-cis,13-trans-prostadienoic acid | dl-11α,15β-trihydroxy-9-oxo-16-m-methylphenoxy-17,20-tetranor-5-cis,13-trans-prostadienoic acid |
| 44 | dl-9α,11α,15β-trihydroxy-16-p-trifluoromethylphenoxy-17,20-tetranor-5-cis,13-trans-prostadienoic acid | dl-11α,15β-dihydroxy-9-oxo-16-p-trifluoromethylphenoxy-17,20-tetranor-5-cis,13-trans-prostadienoic acid |
| 45 | dl-9α,11α,15β-trihydroxy-16-p-methoxyphenoxy-17,20-tetranor-5-cis,13-trans-prostadienoic acid | dl-11α,15β-dihydroxy-9-oxo-16-p-methoxyphenoxy-17,20-tetranor-5-cis,13-trans-prostadienoic acid |
| 46 | dl-9α,11α,15β-trihydroxy-16-o-methoxyphenoxy-17,20-tetranor-5-cis,13-trans-prostadienoic acid | dl-11α,15β-dihydroxy-9-oxo-16-o-methoxyphenoxy-17,20-tetranor-5-cis,13-trans-prostadienoic acid |
| 47 | dl-9α,11α,15β-trihydroxy-16-m-fluorophenoxy-17,20-tetranor-5-cis,13-trans-prostadienoic acid | dl-11α,15β-dihydroxy-9-oxo-16-m-fluorophenoxy-17,20-tetranor-5-cis,13-trans-prostadienoic acid |
| 48 | dl-9α,11α,15β-trihydroxy-16-o-fluorophenoxy-17,20-tetranor-5-cis,13-trans-prostadienoic acid | dl-11α,15β-dihydroxy-9-oxo-16-o-fluorophenoxy-17,20-tetranor-5-cis,13-trans-prostadienoic acid |
| 49 | dl-9α,11α,15β-trihydroxy-16-o-methylphenoxy-17,20-tetranor-5-cis,13-trans-prostadienoic acid | dl-11α,15β-dihydroxy-9-oxo-16-o-methylphenoxy-17,20-tetranor-5-cis,13-trans-prostadienoic acid |
| 50 | dl-9α,11α,15β-trihydroxy-16-m-dimethylaminophenoxy-17,20-tetranor-5-cis,13-trans-prostadienoic acid | dl-11α,15β-dihydroxy-9-oxo-16-m-dimethylaminophenoxy-17,20-tetranor-5-cis,13-trans-prostadienoic acid |
| 51 | dl-9α,11α,15β-trihydroxy-16-(1-naphthyloxy)-17,20-tetranor-5-cis,13-trans-prostadienoic acid | dl-11α,15β-dihydroxy-9-oxo-16-(1-naphthyloxy)-17,20-tetranor-5-cis,13-trans-prostadienoic acid |

-continued

| Example | Starting Compound | 9-Oxo Product |
|---|---|---|
| 52 | dl-9α,11α,15β-trihydroxy-16-(6-methoxy-2-naphthyloxy)-17,20-tetranor-5-cis,13-trans-prostadienoic acid | dl-11α,15β-dihydroxy-9-oxo-16-(6-methoxy-2-naphthyloxy)-17,20-tetranor-5-cis,13-trans-prostadienoic acid |
| 53 | dl-9α,11α,15β-trihydroxy-16-(2,3-dichlorophenoxy)-17,20-tetranor-5-cis,13-trans-prostadienoic acid | dl-11α,15β-dihydroxy-9-oxo-16-(2,3-dichlorophenoxy)-17,20-tetranor-5-cis,13-trans-prostadienoic acid |
| 54 | dl-9α,11α,15β-trihydroxy-16-(3,5-dichlorophenoxy)-17,20-tetranor-5-cis,13-trans-prostadienoic acid | dl-11α,15β-dihydroxy-9-oxo-16-(3,5-dichlorophenoxy)-17,20-tetranor-5-cis,13-trans-prostadienoic acid |
| 55 | dl-9α,11α,15β-trihydroxy-16-m-methoxyphenoxy-17,20-tetranor-5-cis,13-trans-prostadienoic acid | dl-11α,15β-dihydroxy-9-oxo-16-m-methoxyphenoxy-17,20-tetranor-5-cis,13-trans-prostadienoic acid |
| 56 | dl-9α,11α,15β-trihydroxy-16-(5,6,7,8-tetrahydro-2-naphthyloxy)-17,20-tetranor-5-cis,13-trans-prostadienoic acid | dl-11α,15β-dihydroxy-9-oxo-16-(5,6,7,8-tetrahydro-2-naphthyloxy)-17,20-tetranor-5-cis,13-trans-prostadienoic acid |
| 57 | dl-9α,11α,15β-trihydroxy-16-phenoxy-17,20-tetranor-5-cis,13-trans-prostadienoic acid | dl-11α,15β-dihydroxy-9-oxo-16-phenoxy-17,20-tetranor-5-cis,13-trans-prostadienoic acid |

EXAMPLE 58

Preparation of dl-11α,15α-dihydroxy-9-oxo-16-phenoxy-17,20-tetranor-13-trans-prostenoic acid by hydrogenation of dl-11α,15α-dihydro-9-oxo-16-phenoxy-17,20-tetranor-5-cis,13-trans-prostadienoic acid (Example 1)

A solution of 110 mg. of dl-11α,15α-dihydroxy-9-oxo-16-phenoxy-17,20-tetranor-5-cis,13-trans-prostadienoic acid (Example 1) in 0.5 ml. acetone and 0.5 ml. benzene is purged with argon and 11 mg. of tris(triphenylphosphine)rhodium chloride is added. This mixture is stirred under hydrogen at 20–30 psi for 6 hours, or until a TLC (using silver nitrate impregnated silica plate) indicates the absence of any prostadienoic acid. The solvents are removed in vacuo and the oily residue is dissolved in 2 ml. methanol and poured into 10 ml. of 0.2 M sodium phosphate buffer. The mixture is extracted twice with toluene. The aqueous layers are acidified to pH 3 with 2 M citric acid, saturated with sodium chloride, and extracted twice with ether. The extracts are dried with magnesium sulfate and concentrated in vacuo to give 100 mg. of an oil.

This oil is chromatographed on acid washed silica gel to give 40 mg. of dl-11α,15α-dihydroxy-9-oxo-16-phenoxy-17,20-tetranor-13-trans-prostenoic acid; λmax. 3400, 1740–1710, 975 cm$^{-1}$.

EXAMPLES 59–65

Treatment of the $E_2$ compounds of the following table by the method of Example 58 is productive of the $E_1$ compound of the table.

TABLE 2

| Example | $E_2$ Compound | $E_1$ compound |
|---|---|---|
| 59 | Example 10 | dl-11α,15α/β-dihydroxy-9-oxo-16-p-methylphenoxy-17,20-tetranor-13,trans-prostenoic acid |
| 60 | Example 11 | dl-11α,15α-dihydroxy-9-oxo-16-m-methylphenoxy-17,20-tetranor-13-trans-prostenoic acid |
| 61 | Example 22 | dl-11α,15α-dihydroxy-9-oxo-16-(3,5-dimethylphenoxy)-17,20-tetranor-13-trans-prostenoic acid |
| 62 | Example 46 | dl-11α,15α-dihydroxy-9-oxo-16-o-methoxyphenoxy-17,20-tetranor-13-trans-prostenoic acid |
| 63 | Example 20 | dl-11α,15β-dihydroxy-9-oxo-16-o-methylphenoxy-17,20-tetranor-13-trans-prostenoic acid |
| 64 | Example 45 | dl-11α,15β-dihydroxy-9-oxo-16-p-methoxyphenoxy-17,20-tetranor-13-trans-prostenoic acid |
| 65 | Example 50 | dl-11α,15β-dihydroxy-9-oxo-16-m-dimethylaminophenoxy-17,20-tetranor-13-trans-prostenoic acid |

EXAMPLE 66

Preparation of dl-15α-hydroxy-9-oxo-16-phenoxy-17,20-tetranor-5-cis-10,13-trans-prostatrienoic acid A solution of 80 mg. of dl-11α,15α-dihydroxy-9-oxo-16-phenoxy-17,20-tetranor-5-cis-13-trans-prostadienoic acid (Example 1) in 5 ml. of 0.5 N hydrochloric acid in 1:1 water-tetrahydrofuran for 60 hours at 25° C.

The solution is diluted with 100 ml. of benzene and 50 ml. of brine is added. The organic solution is concentrated in vacuo to afford the oily product; λmax: 3400, 1710, 975 cm$^{-1}$, λmax: 217 nm (ε=9000).

EXAMPLES 67–129

The prostaglandin E compound of the table, when submitted to the reaction conditions of Example 66 gives the prostaglandin A product of the table.

TABLE 3

| Example | Starting E Compound | Product A Compound |
|---|---|---|
| 67 | Example 2 | dl-15α-hydroxy-9-oxo-16-benzyloxy-17,20-tetranor-5-cis-10,13-trans-prostatrienoic acid |
| 68 | Example 3 | dl-15α-hydroxy-9-oxo-16-(2-naphthyloxy)-17,20- |

TABLE 3-continued

| Example | Starting E Compound | Product A Compound |
|---|---|---|
| | | tetranor-5-cis,10,13-trans-prostatrienoic acid |
| 69 | Example 4 | dl-15α-hydroxy-9-oxo-16-p-chlorophenoxy-17,20-tetranor-5-cis,10,13-trans-prostatrienoic acid |
| 70 | Example 5 | dl-15α-hydroxy-9-oxo-16-o-chlorophenoxy-17,20-tetranor-5-cis,10,13-trans-prostatrienoic acid |
| 71 | Example 6 | dl-15α-hydroxy-9-oxo-16-o-chlorophenoxy-17,20-tetranor-5-cis-,10,13-trans-prostatrienoic acid |
| 72 | Example 7 | dl-15α-hydroxy-9-oxo-16-(2,4-dichlorophenoxy)-17,20-tetranor-5-cis,10,13-trans-prostatrienoic acid |
| 73 | Example 8 | dl-15α-hydroxy-9-oxo-16-p-bromophenoxy-17,20-tetranor-5-cis,10,13-trans-prostatrienoic acid |
| 74 | Example 9 | dl-15α-hydroxy-9-oxo-16-p-fluorophenoxy-17,20-tetranor-5-cis,10,13-trans-prostatrienoic acid |
| 75 | Example 10 | dl-15α/β-hydroxy-9-oxo-16-p-methylphenoxy-17,20-tetranor-5-cis,10,13-trans-prostatrienoic acid |
| 76 | Example 11 | dl-15α-hydroxy-9-oxo-16-m-methylphenoxy-17,20-tetranor-5-cis,10,13-trans-prostatrienoic acid |
| 77 | Example 12 | dl-15α/β-hydroxy-9-oxo-16-p-t-butylphenoxy-17,20-tetranor-5-cis,10,13-trans-prostatrienoic acid |
| 78 | Example 13 | dl-15α-hydroxy-9-oxo-16-p-trifluoromethylphenoxy-17,20-tetranor-5-cis,10,13-trans-prostatrienoic acid |
| 79 | Example 14 | dl-15α-hydroxy-9-oxo-16-p-methoxyphenoxy-17,20-tetranor-5-cis,10,13-trans-prostatrienoic acid |
| 80 | Example 15 | dl-15α-hydroxy-9-oxo-16-o-methoxyphenoxy-17,20 tetranor-5-cis,10,13-trans-prostatrienoic acid |
| 81 | Example 16 | dl-15αhydroxy-9-oxo-16-m-fluorophenoxy-17,20-tetranor-5-cis-,10,13-trans-prostatrienoic acid |
| 82 | Example 17 | dl-15α-hydroxy-9-oxo-16-o-fluorophenoxy-17,20-tetranor-5-cis,10,13-trans-prostatrienoic acid |
| 83 | Example 18 | dl-15α-hydroxy-9-oxo-16-(3,4-dichlorophenoxy)-17,20-tetranor-5-cis,10,13-trans-prostatrienoic acid |
| 84 | Example 19 | dl-15α-hydroxy-9-oxo-16-(2,5-dichlorophenoxy)-17,20-tetranor-5-cis,10,13-trans-prostatrienoic acid |
| 85 | Example 20 | dl-15α-hydroxy-9-oxo-16-o-methylphenoxy-17,20-tetranor-5-cis,10,13-trans-prostatrienoic acid |
| 86 | Example 21 | dl-15α-hydroxy-9-oxo-16-(2,3-dimethylphenoxy)-17,20-tetranor-5-cis,10,13-trans-prostatrienoic acid |
| 87 | Example 22 | dl-15α-hydroxy-9-oxo-16-(3,5-dimethylphenoxy)-17,20-tetranor-5-cis,10,13-trans-prostatrienoic acid |
| 88 | Example 23 | dl-15α-hydroxy-9-oxo-16-(2-chloro-4-methylphenoxy)-17,20-tetranor-5-cis,10,13-trans-prostatrienoic acid |
| 89 | Example 24 | dl-15α-hydroxy-9-oxo-16-m-dimethylaminophenoxy-17,20-tetranor-5-cis,10,13-trans-prostatrienoic acid |
| 90 | Example 25 | dl-15α-hydroxy-9-oxo-16-(1-naphthyloxy)-17,20-tetranor-5-cis,10,13-trans-prostatrienoic acid |
| 91 | Example 26 | dl-15α-hydroxy-9-oxo-16-(4-chloro-1-naphthyloxy)-17,20-tetranor-5-cis,10,13-trans-prostatrienoic acid |
| 92 | Example 27 | dl-15α-hydroxy-9-oxo-16-(6-methyl-2-naphthyloxy)-17,20-tetranor-5-cis,10,13-trans-prostatrienoic acid |
| 93 | Example 28 | dl-15α-hydroxy-9-oxo-16-(6-methoxy-2-naphthyloxy)-17,20-tetranor-5-cis,10,13-trans-prostatrienoic acid |
| 94 | Example 29 | dl-15α-hydroxy-9-oxo-16-(2,3-dichlorophenoxy)-17,20-tetranor-5-cis,10,13-trans-prostatrienoic acid |
| 95 | Example 30 | dl-15α-hydroxy-9-oxo-16-(2,6-dichlorophenoxy)-17,20-tetranor-5-cis,10,13-trans-prostatrienoic acid |
| 96 | Example 31 | dl-15α-hydroxy-9-oxo-16-(3,5-dichlorophenoxy)-17,20-tetranor-5-cis,10,13-trans-prostatrienoic acid |
| 97 | Example 32 | dl-15α-hydroxy-9-oxo-16-(4-chloro-3-methylphenoxy)-17,20-tetranor-5-cis,10,13-trans-prostatrienoic acid |
| 98 | Example 33 | dl-15α-hydroxy-9-oxo-16-m-methoxyphenoxy-17,20-tetranor-5-cis,10,13,-trans-prostatrienoic acid |
| 99 | Example 34 | dl-15α/β-hydroxy-9-oxo-16-(1-chloro-2-naphthyloxy)-17,20-tetranor-5-cis,10,13-trans-prostatrienoic acid |
| 100 | Example 35 | dl-15-60-hydroxy-9-oxo-16-(5,6,7,8-tetrahydro-2-naphthyloxy)-17,20-tetranor-5-cis,10,13-trans-prostatrienoic acid |
| 101 | Example 36 | dl-15β-hydroxy-9-oxo-16-benzyloxy-17,20-tetranor-5-cis,10,13-trans-prostatrienoic acid |
| 102 | Example 37 | dl-15β-hydroxy-9-oxo-16-(2-naphthyloxy)-17,20-tetranor-5-cis,10,13-trans-prostatrienoic acid |
| 103 | Example 38 | dl-15β-hydroxy-9-oxo-16-p-chlorophenoxy-17,20-tetranor-5-cis,10,13-trans-prostatrienoic acid |
| 104 | Example 39 | dl-15β-hydroxy-9-oxo-16-m-chlorophenoxy-17,20- |

TABLE 3-continued

| Example | Starting E Compound | Product A Compound |
|---|---|---|
| 105 | Example 40 | tetranor-5-cis,10,13-trans-prostatrienoic acid<br>dl-15β-hydroxy-9-oxo-16-o-chlorophenoxy-17,20-tetranor-5-cis,10,13-trans-prostatrienoic acid |
| 106 | Example 41 | dl-15β-hydroxy-9-oxo-16-(2,4-dichlorophenoxy)-17,20-tetranor-5-cis,10,13-trans-prostatrienoic acid |
| 107 | Example 42 | dl-15β-hydroxy-9-oxo-16-p-fluorophenoxy-17,20-tetranor-5-cis,10,13-trans-prostatrienoic acid |
| 108 | Example 43 | dl-15β-hydroxy-9-oxo-16-m-methylphenoxy-17,20-tetranor-5-cis,10,13-trans-prostatrienoic acid |
| 109 | Example 44 | dl-15β-hydroxy-9-oxo-16-p-trifluoromethylphenoxy-17,20-tetranor-5-cis,10,13-trans-prostatrienoic acid |
| 110 | Example 45 | dl-15β-hydroxy-9-oxo-16-p-methoxyphenoxy-17,20-tetranor-5-cis,10,13-trans-prostatrienoic acid |
| 111 | Example 46 | dl-15β-hydroxy-9-oxo-16-o-methoxyphenoxy-17,20-tetranor-5-cis,10,13-trans-prostatrienoic acid |
| 112 | Example 47 | dl-15β-hydroxy-9-oxo-16-m-fluorophenoxy-17,20-tetranor-5-cis,10,13-trans-prostatrienoic acid |
| 113 | Example 48 | dl-15β-hydroxy-9-oxo-16-o-fluorophenoxy-17,20-tetranor-5-cis,10,13-trans-prostatrienoic acid |
| 114 | Example 49 | dl-15β-hydroxy-9-oxo-16-o-methylphenoxy-17,20-tetranor-5-cis,10,13-trans-prostatrienoic acid |
| 115 | Example 50 | dl-15β-hydroxy-9-oxo-16-m-dimethylaminophenoxy-17,20-tetranor-5-cis,10,13-trans-prostatrienoic acid |
| 116 | Example 51 | dl-15β-hydroxy-9-oxo-16-(1-naphthyloxy)-17,20-tetranor-5-cis,10,13-trans-prostatrienoic acid |
| 117 | Example 52 | dl-15β-hydroxy-9-oxo-16-(6-methoxy-2-naphthyloxy)-17,20-tetranor-5-cis,10,13-trans-prostatrienoic acid |
| 118 | Example 53 | dl-15β-hydroxy-9-oxo-16-(2,3-dichlorophenoxy)-17,20-tetranor-5-cis,10,13-trans-prostatrienoic acid |
| 119 | Example 54 | dl-15β-hydroxy-9-oxo-16-(3,5-dichlorophenoxy)-17,20-tetranor-5-cis,10,13-trans-prostatrienoic acid |
| 120 | Example 55 | dl-15β-hydroxy-9-oxo-16-m-methoxyphenoxy-17,20-tetranor-5-cis,10,13-trans-prostatrienoic acid |
| 121 | Example 56 | dl-15β-hydroxy-9-oxo-16-(5,6,7,8-tetrahydro-2-naphthyloxy)-17,20-tetranor-5-cis,10,13-trans-prostatrienoic acid |
| 122 | Example 57 | dl-15β-hydroxy-9-oxo-16-phenoxy-17,20-tetranor-5-cis,10,13-trans-prostatrienoic acid |
| 123 | Example 58 | dl-15α-hydroxy-9-oxo-16-phenoxy-17,20-tetranor-10,13-trans-prostadienoic acid |
| 124 | Example 60 | dl-15α-hydroxy-9-oxo-16-m-methylphenox-17,20-tetranor-10,13-trans-prostadienoic acid |
| 125 | Example 61 | dl-15α-hydroxy-9-oxo-16-(3,5-dimethylphenoxy)-17,20-tetranor-10,13-trans-prostadienoic acid |
| 126 | Example 62 | dl-15β-hydroxy-9-oxo-16-o-methoxyphenoxy-17,20-tetranor-10,13-trans-prostadienoic acid |
| 127 | Example 63 | dl-15α-hydroxy-9-oxo-16-o-methylphenoxy-17,20-tetranor-10,13-trans-prostadienoic acid |
| 128 | Example 64 | dl-15β-hydroxy-9-oxo-16-p-methoxyphenoxy-17,20-tetranor-10,13-trans-prostadienoic acid |
| 129 | Example 65 | dl-15β-hydroxy-9-oxo-16-m-dimethylaminophenoxy-17,20-tetranor-10,13-trans-prostadienoic acid |
| 129a | Example 59 | dl-11α,15α/β-dihydroxy-9-oxo-16-p-methylphenoxy-17,20-tetranor-10,13-trans-prostadienoic acid |

EXAMPLE 130

Preparation of dl-11-deoxy-15α-hydroxy-9-oxo-16-phenoxy-17,20-tetranor-5-cis,13-trans-prostadienoic acid 150 mg. of dl-15α-hydroxy-9-oxo-16-phenoxy-17,20-tetranor-5-cis,10,13-trans-prostatrienoic acid (Example 66) in 10 ml. of ether is esterified with excess diazomethane in ether. Evaporation of the ether gives dl-15α-hydroxy-9-oxo-16-phenoxy-17,20-tetranor-5-cis,10,13-trans-prostatrienoic acid methyl ester.

The crude methyl ester is dissolved in 10 ml. of benzene and 7 ml. of a 1 N solution of acetic anhydride-pyridine in benzene is added. After 24 hours 5 ml. more of 1 N acetic anhydride-piperidine is added and stirred. After an additional 24 hours, 5 ml. more of 1 N acetic anhydride-pyridine is added and stirred 72 hours or until TLC indicates no starting material present. The volume of the reaction is reduced to 10 ml. in vacuo on a rotary evaporator. The reaction product is chromatographed on acid washed silica-gel with ethyl acetate-benzene to provide dl-15α-acetoxy-9-oxo-16-phenoxy-17,20-tetranor-5-cis,10,13-trans-prostatrienoic acid methyl ester as an oil.

The crude methyl ester is dissolved in 3 ml. of ethanol at 0° C. and is treated dropwise with a cold solution of 230 mg. of sodium borohydride in 3 ml. of ethanol containing 0.3 ml. of water. After 15 minutes, 0.25 ml. of acetic acid and 10 ml. of water is added, and the mixture is extracted with 50 ml. of methylene chloride. The organic extract is washed with sodium bicarbonate, dried with magnesium sulfate, and concentrated in vacuo to given an oil.

The crude oil is dissolved in 8 ml. of acetone and cooled to −5° C. Then 0.3 ml. of Jones chromic oxide mixture is added slowly and after 15 minutes 0.1 ml. of isopropanol is added.

After 5 minutes the solution is diluted with 25 ml. of methylene chloride and washed with 20 ml. of water. The methylene chloride is dried with magnesium sulfate and concentrated in vacuo to give the crude mixture as an oil.

The oil is purified on acid washed silica-gel using benzene-ethyl acetate to give dl-15α-acetoxy-11-deoxy-9-oxo-16-phenoxy-17,20-tetranor-5-cis,13-trans-prostadienoic acid methyl ester as an oil.

To 50 mg. of the methyl ester in 2 ml. of methanol is added 1 ml. of 2.5 N aqueous sodium hydroxide. After stirring for 8 hours, the solution is acidified with 30% aqueous sodium dihydrogen phosphate, saturated with sodium chloride, and extracted with ether. The ether extracts are dried with magnesium sulfate and concentrated in vacuo to give dl-11-deoxy-15α-hydroxy-9-oxo-16-phenoxy-17,20-tetranor-5-cis,13-trans-prostadienoic acid; 3400, 1735, 1710, 975 cm$^{-1}$.

EXAMPLES 131-194

Treatment of the A type compounds of the table by the method of Example 130 is productive of the 11-deoxy compounds of the table.

TABLE 4

| Example | Starting Prostaglandin A | 11-Deoxy Product |
|---|---|---|
| 131 | Example 67 | dl-11-deoxy-15α-hydroxy-9-oxo-16-benzyloxy-17,20-tetranor-5-cis,13-trans-prostadienoic acid |
| 132 | Example 68 | dl-11-deoxy-15α-hydroxy-9-oxo-16-(2-naphthyloxy)-17,20-tetranor-5-cis,13-trans-prostadienoic acid |
| 133 | Example 69 | dl-11-deoxy-15α-hydroxy-9-oxo-p-chlorophenoxy-17,20-tetranor-5-cis,13-trans-prostadienoic acid |
| 134 | Example 70 | dl-11-deoxy-15α-hydroxy-9-oxo-16-m-chlorophenoxy-17,20-tetranor-5-cis,13-trans-prostadienoic acid |
| 135 | Example 71 | dl-11-deoxy-15α-hydroxy-9-oxo-16-o-chlorophenoxy-17,20-tetranor-5-cis,13-trans-prostadienoic acid |
| 136 | Example 72 | dl-11-deoxy-15α-hydroxy-9-oxo-16-(2,4-dichlorophenoxy)-17,20-tetranor-5-cis,13-trans-prostadienoic acid |
| 137 | Example 73 | dl-11-deoxy-15α-hydroxy-9-oxo-16-p-bromophenoxy-17,20-tetranor-5-cis,13-trans-prostadienoic acid |
| 138 | Example 74 | dl-11-deoxy-15α-hydroxy-9-oxo-16-p-fluorophenoxy-17,20-tetranor-5-cis,13-trans-prostadienoic acid |
| 139 | Example 75 | dl-11-deoxy-15α/β-hydroxy-9-oxo-16-p-methyphenoxy-17,20-tetranor-5-cis,13-trans-prostadienoic acid |
| 140 | Example 76 | dl-11-deoxy-15α-hydroxy-9-oxo-16-m-methylphenoxy-17,20-tetranor-5-cis,13-trans-prostadienoic acid |
| 141 | Example 77 | dl-11-deoxy-15α/β-hydroxy-9-oxo-16-p-t-butylphenoxy-17,20-tetranor-5-cis,13-trans-prostadienoic acid |
| 142 | Example 78 | dl-11-deoxy-15α-hydroxy-9-oxo-16-p-trifluoromethyl-phenoxy-17,20-tetranor-5-cis,13-trans-prostadienoic acid |
| 143 | Example 79 | dl-11-deoxy-15α-hydroxy-9-oxo-16-p-methoxyphenoxy-17,20-tetranor-5-cis,13-trans-prostadienoic acid |
| 144 | Example 80 | dl-11-deoxy-15α-hydroxy-9-oxo-16-o-methoxyphenoxy-17,20-tetranor-5-cis,13-trans-prostadienoic acid |
| 145 | Example 81 | dl-11-deoxy-15α-hdroxy-9-oxo-16-m-fluorophenoxy-17,20-tetranor-5-cis,13-trans-prostadienoic acid |
| 146 | Example 82 | dl-11-deoxy-15α-hydroxy-9-oxo-16-o-fluorophenoxy-17,20-tetranor-5-cis,13-trans-prostadienoic acid |
| 147 | Example 83 | dl-11-deoxy-15α-hydroxy-9-oxo-16-(3,4-dichlorophenoxy)-17,20-tetranor-5-cis,13-trans-prostadienoic acid |
| 148 | Example 84 | dl-11-deoxy-15α-hydroxy-9-oxo-16-(2,5-dichlorophenoxy)-17,20-tetranor-5-cis,13-trans-prostadienoic acid |
| 149 | Example 85 | dl-11-deoxy-15α-hydroxy-9-oxo-16-o-methylphenoxy-17,20-tetranor-5-cis,13-trans-prostadienoic acid |
| 150 | Example 86 | dl-11-deoxy-15α-hydroxy-9-oxo-16-(2,3-dimethyl-phenoxy)-17,20-tetranor-5-cis,13-trans-prostadienoic acid |
| 151 | Example 87 | dl-11-deoxy-15α-hydroxy-9-oxo-16-(3,5-dimethyl-phenoxy)-17,20-tetranor-5-cis,13-trans-prostadienoic acid |
| 152 | Example 88 | dl-11-deoxy-15α-hydroxy-9-oxo-16-(2-chloro-4-methyl-phenoxy)-17,20-tetranor-5-cis,13-trans-prostadienoic acid |
| 153 | Example 89 | dl-11-deoxy-15α-hydroxy-9-oxo-16-m-dimethylaminophenoxy-17,20-tetranor-5-cis,13-trans-prostadienoic acid |
| 154 | Example 90 | dl-11-deoxy-15α-hydroxy-9-oxo-16-(1-naphthyloxy)-17,20-tetranor-5-cis,13-trans-prostadienoic acid |
| 155 | Example 91 | dl-11-deoxy-15α-hydroxy-9-oxo-16-(4-chloro-1-naphthyloxy)-17,20-tetranor-5-cis,13-trans-prosdienoic acid |
| 156 | Example 92 | dl-11-deoxy-15α-hydroxy-9-oxo-16-(6-methyl-2-naphthyloxy)-17,20-tetranor-5-cis,13-trans-prostadienoic acid |
| 157 | Example 93 | dl-11-deoxy-15α-hydroxy-9-oxo-16-(6-methoxy-2-naphthyloxy)-17,20-tetranor-5-cis,13-trans-prostadienoic acid |
| 158 | Example 94 | dl-11-deoxy-15α-hydroxy-9-oxo-16-(2,3-dichlorophenoxy)-17,20-tetranor-5-cis,13-trans-prostadienoic acid |
| 159 | Example 95 | dl-11-deoxy-15α-hydroxy-9-oxo-16-(2,6-dichlorophenoxy)-17,20-tetranor-5-cis,13-trans-prostadienoic acid |
| 160 | Example 96 | dl-11-deoxy-15α-hydroxy-9-oxo-16-(3,5-dichlorophenoxy)-17,20-tetranor-5-cis,13-trans-prostadienoic acid |
| 161 | Example 97 | dl-11-deoxy-15α-hydroxy-9-oxo-16-(4-chloro-3-methyl-phenoxy)-17,20-tetranor-5-cis,13-trans-prostadienoic acid |
| 162 | Example 98 | dl-11-deoxy-15α-hydroxy-9-oxo-16-m-methoxyphenoxy-17,20-tetranor-5-cis,13-trans-prostadienoic acid |

TABLE 4-continued

| Example | Starting Prostaglandin A | 11-Deoxy Product |
|---|---|---|
| 163 | Example 99 | dl-11-deoxy-15α-hydroxy-9-oxo-16-(1-chloro-2-naphthyloxy)-17,20-tetranor-5-cis,13-trans-prostadienoic acid |
| 164 | Example 100 | dl-11-deoxy-15α-hydroxy-9-oxo-16-(5,6,7,8-tetrahydro-2-napthyloxy)17,20-tetranor-5-cis,13-trans-prostadienoic acid |
| 165 | Example 101 | dl-11-deoxy-15β-hydroxy-9-oxo-16-benzyloxy-17,20-tetranor-5-cis,13-trans-prostadienoic acid |
| 166 | Example 102 | dl-11-deoxy-15β-hydroxy-9-oxo-16-(2-naphthyloxy)-17,20-tetranor-5-cis,13-trans-prostadienoic acid |
| 167 | Example 103 | dl-11-deoxy-15β-hydroxy-9-oxo-16-p-chlorophenoxy-17,20-tetranor-5-cis,13-trans-prostadienoic acid |
| 168 | Example 104 | dl-11-deoxy-15β-hydroxy-9-oxo-16-m-chlorophenoxy-17,20-tetranor-5-cis,13-trans-prostadienoic acid |
| 169 | Example 105 | dl-11-deoxy-15β-hydroxy-9-oxo-16-o-chlorophenoxy-17,20-tetranor-5-cis,13-trans-prostadienoic acid |
| 170 | Example 106 | dl-11-deoxy-15β-hydroxy-9-oxo-16-(2,4-dichlorophenoxy)-17,20-tetranor-5-cis,13-trans-prostadienoic acid |
| 171 | Example 107 | dl-11-deoxy-15β-hydroxy-9-oxo-16-p-fluorophenoxy-17,20-tetranor-5-cis,13-trans-prostadienoic acid |
| 172 | Example 108 | dl-11-deoxy-15β-hydroxy-9-oxo-16-m-methylphenoxy-17,20-tetranor-5-cis,13-trans-prostadienoic acid |
| 173 | Example 109 | dl-11-deoxy-15β-hydroxy-9-oxo-16-p-trifluoromethylphenoxy-17,20-tetranor-5-cis,13-trans-prostadienoic acid |
| 174 | Example 110 | dl-11-deoxy-15β-hydroxy-9-oxo-16-p-methoxyphenoxy-17,20-tetranor-5-cis,13-trans-prostadienoic acid |
| 175 | Example 111 | dl-11-deoxy-15β-hydroxy-9-oxo-16-m-methoxyphenoxy-17,20-tetranor-5-cis,13-trans-prostadienoic acid |
| 176 | Example 112 | dl-11-deoxy-15β62-hydroxy-9-oxo-16-m-fluorophenoxy-17,20-tetranor-5-cis,13-trans-prostadienoic acid |
| 177 | Example 113 | dl-11-deoxy-15β-hydroxy-9-oxo-16-o-fluorophenoxy-17,20-tetranor-5-cis,13-trans-prostadienoic acid |
| 178 | Example 114 | dl-11-deoxy-15β-hydroxy-9-oxo-16-o-methylphenoxy-17,20-tetranor-5-cis,13-trans-prostadienoic acid |
| 179 | Example 115 | dl-11-deoxy-15β-hydroxy-9-oxo-16-m-dimethylaminophenoxy-17,20-tetranor-5-cis,13-trans-prostadienoic acid |
| 180 | Example 116 | dl-11-deoxy-15β-hydroxy-9-oxo-16-(1-naphthyloxy)-17,20-tetranor-5-cis,13-trans-prostadienoic acid |
| 181 | Example 117 | dl-11-deoxy-15β-hydroxy-9-oxo-16-(6-methoxy-2-naphthyloxy)-17,20-tetranor-5-cis,13-trans-prostadienoic acid |
| 182 | Example 118 | dl-11-deoxy-15β-hydroxy-9-oxo-16-(2,3-dichlorophenoxy)-17,20-tetranor-5-cis,13-trans-prostadienoic acid |
| 183 | Example 119 | dl-11-deoxy-15β-hydroxy-9-oxo-16-(3,5-dichlorophenoxy)-17,20-tetranor-5-cis,13-trans-prostadienoic acid |
| 184 | Example 120 | dl-11-deoxy-15β-hydroxy-9-oxo-16-m-methoxyphenoxy-17,20-tetranor-5-cis,13-trans-prostadienoic acid |
| 185 | Example 121 | dl-11-deoxy-15β-hydroxy-9-oxo-16-(5,6,7,8-tetrahydro-2-naphthyloxy)-17,20-tetranor-5-cis,13-trans-prostadienoic acid |
| 186 | Example 122 | dl-11-deoxy-15β-hydroxy-9-oxo-16-phenoxy-17,20-tetranor-5-cis,13-trans-prostadienoic acid |
| 187 | Example 123 | dl-11-deoxy-15α-hydroxy-9-oxo-16-phenoxy-17,20-tetranor-13-trans-prostenoic acid |
| 188 | Example 129a | dl-11-deoxy-15α/β-hydroxy-9-oxo-16-p-methylphenoxy-17,20-tetranor-13-trans-prostenoic acid |
| 189 | Example 124 | dl-11-deoxy-15α-hydroxy-9-oxo-16-m-methylphenoxy-17,20-tetranor-13-trans-prostenoic acid |
| 190 | Example 125 | dl-11-deoxy-15α-hydroxy-9-oxo-16-(3,5-dimethylphenoxy)-17,20-tetranor-13-trans-prostenoic acid |
| 191 | Example 126 | dl-11-deoxy-15β-hydroxy-9-oxo-16-o-methoxyphenoxy-17,20-tetranor-13-trans-prostenoic acid |
| 192 | Example 127 | dl-11-deoxy-15α-hydroxy-9-oxo-16-o-methylphenoxy-17,20-tetranor-13-trans-prostenoic acid |
| 193 | Example 128 | dl-11-deoxy-15β-hydroxy-9-oxo-16-p-methoxyphenoxy-17,20-tetranor-13-trans-prostenoic acid |
| 194 | Example 129 | dl-11-deoxy-15β-hydroxy-9-oxo-16-m-dimethylaminophenoxy-17,20-tetranor-13-trans-prostenoic acid |

EXAMPLE 195

Preparation of dl-11-deoxy-9-oxo-15α-hydroxy-16-phenoxy-17,20-tetranor-prostanoic acid A solution of 900 mg. of dl-11-deoxy-9-oxo-15α-hydroxy-16-phenoxy-17,20-tetranor-13-trans-prostenoic acid (Example 187) in 1 ml. of acetone and 1 ml. of benzene was purged with nitrogen and 0.1 gm. of tris(triphenylphosphine)rhodium chloride is added. The mixture is shaken under 20–30 pounds of hydrogen for 12 hours. The mixture is diluted with 50 ml. of 5% aqueous sodium carbonate and extracted with 10 ml. of toluene. The aqueous solution is acidified to pH 4 with 2 N aqueous hydrochloric acid saturated with sodium chloride, and extracted twice with 50 ml. of ether. The ether is dried with magnesium sulfate and concentrated in vacuo to give dl-11-deoxy-9-oxo-16-phenoxy-17,20-tetranorprostanoic acid; max. 3400, 1735 cm$^{-1}$.

EXAMPLES 196–202

Hydrogenation of the $E_1$ compounds of the following table by the procedure of Example 195 is productive of the 13-dihydro compounds of the table.

TABLE 5

| Example | Starting 13-trans-prostenoic acid | Product Prostanoic Acid |
|---|---|---|
| 196 | Example 188 | dl-11-deoxy-15α/β-hydroxy-9-oxo-16-p-methylphenoxy-17,20-tetranor-prostanoic acid |
| 197 | Example 189 | dl-11-deoxy-15α-hydroxy-9-oxo-16-m-methylphenoxy-17,20-tetranor-prostanoic acid |
| 198 | Example 190 | dl-11-deoxy-15α-hydroxy-9-oxo-16-(3,5-dimethylphenoxy)-17,20-tetranor-prostanoic acid |
| 199 | Example 191 | dl-11-deoxy-15β-hydroxy-9-oxo-16-o-methoxyphenoxy-17,20-tetranor-prostanoic acid |
| 200 | Example 192 | dl-11-deoxy-15α-hydroxy-9-oxo-16-o-methylphenoxy-17,20-tetranor-prostanoic acid |
| 201 | Example 193 | dl-11-deoxy-15β-hydroxy-9-oxo-16-p-methoxyphenoxy-17,20-tetranor-prostanoic acid |
| 202 | Example 194 | dl-11-deoxy-15βhydroxy-9-oxo-16-m-dimethylaminophenoxy-17,20-tetranor-prostanoic acid |

EXAMPLE 203

Preparation of dl-11-deoxy-9α,15α-dihydroxy-16-phenoxy-17,20-tetranor-5-cis,13-trans-prostadienoic acid To 5 ml. of a −78° C. solution of 1 M lithium-tri-sec-butylborohydride in tetrahydrofuran is added slowly a cold solution of 600 mg. of dl-11-deoxy-15α-hydroxy-9-oxo-16-phenoxy-17,20-tetranor-5-cis,13-trans-prostadienoic acid in 5 ml. of tetrahydrofuran. After 20 minutes at −78° C., 2 ml. of 2.5 N aqueous sodium hydroxide is added and the solution is stirred at a 30° C. bath for 40 minutes. The solution is diluted with 10 ml. of water and extracted three times with 20 ml. of ether.

The aqueous solution is acidified to pH 4 with 6 N hydrochloric acid, saturated with sodium chloride and extracted twice with 50 ml. of ether. The ether extracts are combined, dried with magnesium sulfate and concentrated in vacuo to give dl-11-deoxy-9α,15α-dihydroxy-16-phenoxy-17,20-tetranor-5-cis,13-trans-prostadienoic acid; λmax. 3400, 1710, 975 cm$^{-1}$.

EXAMPLES 204–272

Treatment of the 9-oxo compounds of the following table by the method of Example 203 is productive of the 9α-hydroxy compounds of the table.

TABLE 6

| Example | 9-Oxo-Compound | 9α-Hydroxy Product |
|---|---|---|
| 204 | Example 131 | dl-11-deoxy-9α,15α-dihydroxy-16-benzyl-17,20-tetranor-5-cis,13-trans-prostadienoic acid |
| 205 | Example 132 | dl-11-deoxy-9α,15α-dihydroxy-16-(2-naphthyloxy)-17,20-tetranor-5-cis,13-trans-prostadienoic acid |
| 206 | Example 133 | dl-11-deoxy-9α,15α-dihydroxy-16-p-chlorophenoxy-17,20-tetranor-5-cis,13-trans-prostadienoic acid |
| 207 | Example 134 | dl-11-deoxy-9α,15α-dihydroxy-16-m-chlorophenoxy-17,20-tetranor-5-cis,13-trans-prostadienoic acid |
| 208 | Example 135 | dl-11-deoxy-9α,15α-dihydroxy-16-o-chlorophenoxy-17,20-tetranor-5-cis,13-trans-prostadienoic acid |
| 209 | Example 136 | dl-11-deoxy-9α,15α-dihydroxy-16-(2,4-dichlorophenoxy)-17,20-tetranor-5-cis,13-trans-prostadienoic acid |
| 210 | Example 137 | dl-11-deoxy-9α,15α-dihydroxy-16-p-bromophenoxy-17,20-tetranor-5-cis,13-trans-prostadienoic acid |
| 211 | Example 138 | dl-11-deoxy-9α,15α-dihydroxy-16-p-fluorophenoxy-17,20-tetranor-5-cis,13-trans-prostadienoic acid |
| 212 | Example 139 | dl-11-deoxy-9α,15α/β-dihydroxy-16-p-methylphenoxy-17,20-tetranor-5-cis,13-trans-prostadienoic acid |
| 213 | Example 140 | dl-11-deoxy-9α,15α-dihydroxy-16-m-methylphenoxy-17,20-tetranor-5-cis,13-trans-prostadienoic acid |
| 214 | Example 141 | dl-11-deoxy-9α,15α/β-dihydroxy-16-p-t-butylphenoxy-17,20-tetranor-5-cis,13-trans-prostadienoic acid |
| 215 | Example 142 | dl-11-deoxy-9α,15α-dihydroxy-16-p-trifluoromethylphenoxy-17,20-tetranor-5-cis,13-trans-prostadienoic acid |
| 216 | Example 143 | dl-11-deoxy-9α,15α-dihydroxy-16-p-methoxyphenoxy-17,20-tetranor-5-cis,13-trans-prostadienoic acid |
| 217 | Example 144 | dl-11-deoxy-9α,15α-dihydroxy-16-o-methoxyphenoxy-17,20-tetranor-5-cis,13-trans-prostadienoic acid |
| 218 | Example 145 | dl-11-deoxy-9α,15α-dihydroxy-16-m-fluorophenoxy-17,20-tetranor-5-cis,13-trans-prostadienoic acid |
| 219 | Example 146 | dl-11-deoxy-9α,15α-dihydroxy-16-o-fluorophenoxy-17,20-tetranor-5-cis,13-trans-prostadienoic acid |
| 220 | Example 147 | dl-11-deoxy-9α,15α-dihydroxy-16-(3,4-dichlorophenoxy)-17,20-tetranor-5-cis,13-trans-prostadienoic acid |
| 221 | Example 148 | dl-11-deoxy-9α,15α-dihydroxy-16-(2,5-dichlorophenoxy)-17,20-tetranor-5-cis,13-trans-prostadienoic acid |
| 222 | Example 149 | dl-11-deoxy-9α,15α-dihydroxy-16-o-methylphenoxy-17,20-tetranor-5-cis,13-trans-prostadienoic acid |
| 223 | Example 150 | dl-11-deoxy-9α,15α-dihydroxy-16-(2,3-dimethylphenoxy)-17,20-tetranor-5-cis,13-trans-prostadienoic acid |
| 224 | Example 151 | dl-11-deoxy-11α,15α-dihydroxy-16-(3,5-dimethylphenoxy)- |

TABLE 6-continued

| Example | 9-Oxo-Compound | 9α-Hydroxy Product |
|---|---|---|
| | | 17,20-tetranor-5-cis,13-trans-prostadienoic acid |
| 225 | Example 152 | dl-11-deoxy-11α,15α-dihydroxy-16-(2-chloro-4-methyl-phenoxy)-17,20-tetranor-5-cis,13-trans-prostadienoic acid |
| 226 | Example 153 | dl-11-deoxy-11α,15α-dihydroxy-16-m-dimethylamino-phenoxy-17,20-tetranor-5-cis,13-trans-prostadienoic acid |
| 227 | Example 154 | dl-11-deoxy-11α,15α-dihydroxy-16-(1-napthyloxy)-17,20-tetranor-5-cis,13-trans-prostadienoic acid |
| 228 | Example 155 | dl-11-doexy-9α,15α-dihydroxy-16-(4-chloro-l-napthyloxy)-17,20-tetranor-5-cis,13-trans-prostadienoic acid |
| 229 | Example 156 | dl-11-deoxy-9α,15α-dihydroxy-16-(6-methyl-2-naphthyloxy)-17,20-tetranor-5-cis,13-trans-prostadienoic acid |
| 230 | Example 157 | dl-11-deoxy-9α,15α-dihydroxy-16-(6-methoxy-2-naphthyloxy)-17,20-tetranor-5-cis,13-trans-prostadienoic acid |
| 231 | Example 158 | dl-11-deoxy-9α,15α-dihydroxy-16-(2,3-dichlorophenoxy)-17,20-tetranor-5-cis,13-trans-prostadienoic acid |
| 232 | Example 159 | dl-11-deoxy-9α,15α-dihydroxy-16-(2,6-dichlorophenoxy)-17,20-tetranor-5-cis,13-trans-prostadienoic acid |
| 233 | Example 160 | dl-11-deoxy-9α,15αdihydroxy-16-(3,5-dichlorophenoxy)-17,20-tetranor-5-cis,13-trans-prostadienoic acid |
| 234 | Example 161 | dl-11-deoxy-9α,15α-dihydroxy-16-(4-chloro-3-methyl-phenoxy)-17,20-tetranor-5-cis,13-trans-porstadienoic acid |
| 235 | Example 162 | dl-11-deoxy-9α,15α-dihydroxy-16-m-methoxyphenoxy-17,20-tetranor-5-cis,13-trans-prostadienoic acid |
| 236 | Example 163 | dl-11-deoxy-9α,15α/β-dihydroxy-16-(1-chloro-2-naphthyloxy)-17,20-tetranor-5-cis,13-trans-prostadienoic acid |
| 237 | Example 164 | dl-11-deoxy-9α,15α-dihydroxy-16-(5,6,7,8-tetrahydro-2-napthyloxy)-17,20-tetranor-5-cis,13-trans-prostadienoic acid |
| 238 | Example 165 | dl-11-deoxy-9α,15β-dihydroxy-16-benzyloxy-17,20-tetranor-5-cis,13-trans-prostadienoic acid |
| 239 | Example 166 | dl-11-deoxy-9α,15β-dihydroxy-16-(2-napthyloxy)-17,20-tetranor-5-cis,13-trans-prostadienoic acid |
| 240 | Example 167 | dl-11-deoxy-9α,15β-dihydroxy-16-p-chlorophenoxy-17,20-tetranor-5-cis,13-trans-prostadienoic acid |
| 241 | Example 168 | dl-11-deoxy-9α,15β-dihydroxy-16-m-chlorophenoxy-17,20-tetranor-5-cis,13-trans-prostadienoic acid |
| 242 | Example 169 | dl-11-deoxy-9α,15β-dihydroxy-16-o-chlorophenoxy-17,20-tetranor-5-cis,13-trans-prostadienoic acid |
| 243 | Example 170 | dl-11-deoxy-9α,15β-dihydroxy-16-(2,4-dichlorophenoxy)-17,20-tetranor-5-cis,13-trans-prostadienoic acid |
| 244 | Example 171 | dl-11-deoxy-9α,15β-dihydroxy-16-p-fluorophenoxy-17,20-tetranor-5-cis,13-trans-prostadienoic acid |
| 245 | Example 172 | dl-11-deoxy-9α,15β-dihydroxy-16-m-methylphenoxy-17,20-tetranor-5-cis,13-trans-prostadienoic acid |
| 246 | Example 173 | dl-11-deoxy-9α,15β-dihydroxy-16-p-trifluoromethyl-phenoxy-17,20-tetranor-5-cis,13-trans-prostadienoic acid |
| 247 | Example 174 | dl-11-deoxy-9α,15β-dihydroxy-16-p-methoxyphenoxy-17,20-tetranor-5-cis,13-trans-prostadienoic acid |
| 248 | Example 175 | dl-11-deoxy-9α,15β-dihydroxy-16-o-methoxyphenoxy-17,20-tetranor-5-cis,13-trans-prostadienoic acid |
| 249 | Example 176 | dl-11-deoxy-9α,15β-dihydroxy-16-m-fluorophenoxy-17,20-tetranor-5-cis,13-trans-prostadienoic acid |
| 250 | Example 177 | dl-11-deoxy-9α,15β-dihydroxy-16-o-fluorophenoxy-17,20-tetranor-5-cis,13-trans-prostadienoic acid |
| 251 | Example 178 | dl-11-deoxy-9α,15β-dihydroxy-16-o-methylphenoxy-17,20-tetranor-5-cis,13-trans-prostadienoic acid |
| 252 | Example 179 | dl-11-deoxy-9α,15β-dihydroxy-16-m-dimethylamino-phenoxy-17,20-tetranor-5-cis,13-trans-prostadienoic acid |
| 253 | Example 180 | dl-11-deoxy-9α,15β-dihydroxy-16-(1-naphthyloxy)-17,20-tetranor-5-cis,13-trans-prostadienoic acid |
| 254 | Example 181 | dl-11-deoxy-9α,15β-dihydroxy-16-(6-methoxy-2-napthyloxy)-17,20-tetranor-5-cis,13-trans-prostadienoic acid |
| 255 | Example 182 | dl-11-deoxy-9α,15β-dihydroxy-16-(2,3-dichlorophenoxy)-17,20-tetranor-5-cis,13-trans-prostadienoic acid |
| 256 | Example 183 | dl-11-deoxy-9α,15β-dihydroxy-16-(3,5-dichlorophenoxy)-17,20-tetranor-5-cis,13-trans-prostadienoic acid |
| 257A | Example 184 | dl-11-deoxy-9α,15β-dihydroxy-16-m-methoxyphenoxy-17,20-tetranor-5-cis,13-trans-prostadienoic acid |
| 257B | Example 185 | dl-11-deoxy-9α,15β-dihydroxy-16-(5,6,7,8-tetrahydro-2-naphthyloxy)-17,20-tetranor-5-cis,13-trans-prostadienoic acid |
| 257C | Example 186 | dl-11-deoxy-9α,15β-dihydroxy-16-phenoxy-17,20-tetranor-5-cis,13-trans-prostadienoic acid |
| 258 | Example 187 | dl-11-deoxy-9α,15β-dihydroxy-16-phenoxy-17,20-tetranor-13-trans-prostenoic acid |
| 259 | Example 189 | dl-11-deoxy-9α,15α-dihydroxy-16-m-methylphenoxy-17,20-tetranor-13-trans-prostenoic acid |

TABLE 6-continued

| Example | 9-Oxo-Compound | 9α-Hydroxy Product |
|---|---|---|
| 260 | Example 190 | dl-11-deoxy-9α,15α-dihydroxy-16-(3,5-dimethylphenoxy)-17,20-tetranor-13-trans-prostenoic acid |
| 261 | Example 191 | dl-11-deoxy-9α,15β-dihydroxy-16-o-methoxyphenoxy-17,20-tetranor-13-trans-prostenoic acid |
| 262 | Example 192 | dl-11-deoxy-9α,15α-dihydroxy-16-o-methylphenoxy-17,20-tetranor-13-trans-prostenoic acid |
| 263 | Example 193 | dl-11-deoxy-9α,15β-dihydroxy-16-p-methoxyphenoxy-17,20-tetranor-13-trans-prostenoic acid |
| 264 | Example 194 | dl-11-deoxy-9α,15β-dihydroxy-16-m-dimethylaminophenoxy-17,20-tetranor-13-trans-prostenoic acid |
| 265 | Example 195 | dl-11-deoxy-9α,15α-dihydroxy-16-phenoxy-17,20-tetranor-prostanoic acid |
| 266 | Example 196 | dl-11-deoxy-9α,15α/β-dihydroxy-16-p-methylphenoxy-17,20-tetranor-13-trans-prostenoic acid |
| 267 | Example 197 | dl-11-deoxy-9α,15α-dihydroxy-16-m-methylphenoxy-17,20-tetranor-13-trans-prostenoic acid |
| 268 | Example 198 | dl-11-deoxy-9α,15α-dihydroxy-16-(3,5-dimethylphenoxy)-17,20-tetranor-13-trans-prostenoic acid |
| 269 | Example 199 | dl-11-deoxy-9α,15β-dihydroxy-16-o-methoxyphenoxy-17,20-tetranor-13-trans-prostenoic acid |
| 270 | Example 200 | dl-11-deoxy-9α,15α-dihydroxy-16-o-methylphenoxy-17,20-tetranor-13-trans-prostenoic acid |
| 271 | Example 201 | dl-11-deoxy-9α,15β-dihydroxy-16-p-methoxyphenoxy-17,20-tetranor-13-trans-prostenoic acid |
| 272 | Example 202 | dl-11-deoxy-9α,15β-dihydroxy-16-m-dimethylaminophenoxy-17,20-tetranor-13-trans-prostenoic acid |

EXAMPLE 273

Preparation of dl-11-deoxy-9α/β,15α-dihydroxy-16-phenoxy-17,20-tetranor-5-cis,13-trans-prostadienoic acid and separation of the 9α and 9β components To a 0° C. solution of 500 mg. of dl-11-deoxy-15α-hydroxy-9-oxo-16-phenoxy-17,20-tetranor-5-cis,13-trans-prostadienoic acid in 10 ml. of ethanol is added 100 mg. of sodium borohydride. After 30 minutes the solution is diluted with 50 ml. of saturated aqueous ammonium chloride and extracted twice with 50 ml. of ether. The ether is dried with magnesium sulfate and concentrated in vacuo to give a nearly 1:1 mixture of the 9α and 9β diols.

The diol mixture is placed onto a dry column of acid washed silica and developed with ethyl acetate-benzene.

The high Rf compound is isolated and is dl-11-deoxy-9α,15α-dihydroxy-16-phenoxy-17,20-tetranor-5-cis,13-trans-prostadienoic acid. The lower Rf, more polar isomer, is dl-11-deoxy-9β,15α-dihydroxy-16-phenoxy-17,20-tetranor-5-cis,13-trans-prostadienoic acid; the infrared spectrum of each is identical: 3400, 1700, 975 cm$^{-1}$.

EXAMPLES 274–345

Treatment of the 9-oxo compounds of the following table with sodium borohydride followed by separation by the method of Example 273 is productive of the separated 9,15-diols of the table.

TABLE 7

| Example | 9-Oxo Compound | Product 9,15-Diols |
|---|---|---|
| 274 | Example 131 | dl-11-deoxy-9α/β,15α-dihydroxy-16-benzyloxy-17,20-tetranor-5-cis,13-trans-prostadienoic acid |
| 275 | Example 132 | dl-11-deoxy-9α/β,15α-dihydroxy-16-(2-naphthyloxy)-17,20-tetranor-5-cis,13-trans-prostadienoic acid |
| 276 | Example 133 | dl-11-deoxy-9α/β,15α-dihydroxy-16-p-chlorophenoxy-17,20-tetranor-5-cis,13-trans-prostadienoic acid |
| 277 | Example 134 | dl-11-deoxy-9α/β,15α-dihydroxy-16-m-chlorophenoxy-17,20-tetranor-5-cis,13-trans-prostadienoic acid |
| 278 | Example 135 | dl-11-deoxy-9α/β,15α-dihydroxy-16-o-chlorophenoxy-17,20-tetranor-5-cis,13-trans-prostadienoic acid |
| 279 | Example 136 | dl-11-deoxy-9α/β,15α-dihydroxy-16-(2,4-dichlorophenoxy)-17,20-tetranor-5-cis,13-trans-prostadienoic acid |
| 280 | Example 137 | dl-11-deoxy-9α/β,15α-dihydroxy-16-p-bromophenoxy-17,20-tetranor-5-cis,13-trans-prostadienoic acid |
| 281 | Example 138 | dl-11-deoxy-9α/β,15α-dihydroxy-16-p-fluorophenoxy-17,20-tetranor-5-cis,13-trans-prostadienoic acid |
| 282 | Example 139 | dl-11-deoxy-9α/β,15α/β-dihydroxy-16-p-methylphenoxy-17,20-tetranor-5-cis,13-trans-prostadienoic acid |
| 283 | Example 140 | dl-11-deoxy-9α,15α-dihydroxy-16-m-methylphenoxy-17,20-tetranor-5-cis,13-trans-prostadienoic acid |
| 284 | Example 141 | dl-11-deoxy-9α,15α/β-dihydroxy-16-p-t-butylphenoxy-17,20-tetranor-5-cis,13-trans-prostadienoic acid |
| 285 | Example 142 | dl-11-deoxy-9α,15α-dihydroxy-16-p-trifluoromethyl-phenoxy-17,20-tetranor-5-cis,13-trans-prostadienoic acid |
| 286 | Example 143 | dl-11-deoxy-9α/β,15α-dihydroxy-16-p-methoxyphenoxy-17,20-tetranor-5-cis,13-trans-prostadienoic acid |
| 287 | Example 144 | dl-11-deoxy-9α/β,15α-dihydroxy-16-o-methoxyphenoxy-17,20-tetranor-5-cis,13-trans-prostadienoic acid |
| 288 | Example 145 | dl-11-deoxy-9α/β,15α-dihydroxy-16-m-fluorophenoxy-17,20- |

TABLE 7-continued

| Example | 9-Oxo Compound | Product 9,15-Diols |
|---|---|---|
| | | tetranor-5-cis,13-trans-prostadienoic acid |
| 289 | Example 146 | dl-11-deoxy-9α/β,15α-dihydroxy-16-o-fluorophenoxy-17,20-tetranor-5-cis,13-trans-prostadienoic acid |
| 290 | Example 147 | dl-11-deoxy-9α/β,15α-dihydroxy-16-(3,4-dichlorophenoxy)-17,20-tetranor-5-cis,13-trans-prostadienoic acid |
| 291 | Example 148 | dl-11-deoxy-9α/β,15α-dihydroxy-16-(2,5-dichlorophenoxy)-17,20-tetranor-5-cis,13-trans-prostadienoic acid |
| 292 | Example 149 | dl-11-deoxy-9α/β,15α-dihydroxy-16-o-methylphenoxy-17,20-tetranor-5-cis,13-trans-prostadienoic acid |
| 293 | Example 150 | dl-11-deoxy-9α/β,15α-dihydroxy-16-(2,3-dimethylphenoxy)-17,20-tetranor-5-cis,13-trans-prostadienoic acid |
| 294 | Example 151 | dl-11-deoxy-9α/β,15α-dihydroxy-16-(3,5-dimethylphenoxy)-17,20-tetranor-5-cis,13-trans-prostadienoic acid |
| 295 | Example 152 | dl-11-deoxy-9α/β,15α-dihydroxy-16-(2-chloro-4-methyl-phenoxy)-17,20-tetranor-5-cis,13-trans-prostadienoic acid |
| 296 | Example 153 | dl-11-deoxy-9α/β,15α-dihydroxy-16-m-dimethylamino-phenoxy-17,20-tetranor-5-cis,13-trans-prostadienoic acid |
| 297 | Example 154 | dl-11-deoxy-9α/β,15α-dihydroxy-16-(1-naphthyloxy)-17,20-tetranor-5-cis,13-trans-prostadienoic acid |
| 298 | Example 155 | dl-11-deoxy-9α/β,15α-dihydroxy-16-(4-chloro-1-naphthyl-oxy)-17,20-tetranor-5-cis,13-trans-prostadienoic acid |
| 299 | Example 156 | dl-11-deoxy-9α/β,15α-dihydroxy-16-(6-methyl-2-naphthyl-oxy)-17,20-tetranor-5-cis,13-trans-prostadienoic acid |
| 300 | Example 157 | dl-11-deoxy-9α/β,15α-dihydroxy-16-(6-methoxy-2-naphthyl-oxy)-17,20-tetranor-5-cis,13-trans-prostadienoic acid |
| 301 | Example 158 | dl-11-deoxy-9α,/β,15α-dihydroxy-16-(2,3-dichlorophenoxy)-17,20-tetranor-5-cis,13-trans-prostadienoic acid |
| 302 | Example 159 | dl-11-deoxy-9α/β,15α-dihydroxy-16-(2,6-dichlorophenoxy)-17,20-tetranor-5-cis,13-trans-prostadienoic acid |
| 303 | Example 160 | dl-11-deoxy-9α/β,15α-dihydroxy-16-(3,5-dichlorophenoxy)-17,20-tetranor-5-cis,13-trans-prostadienoic acid |
| 304 | Example 161 | dl-11-deoxy-9α/β,15α-dihydroxy-16-(4-chloro-3-methyl-phenoxy)-17,20-tetranor-5-cis,13-trans-prostadienoic acid |
| 305 | Example 162 | dl-11-deoxy-9α/β,15α-dihydroxy-16-m-methoxyphenoxy-17,20-tetranor-5-cis,13-trans-prostadienoic acid |
| 306 | Example 163 | dl-11-deoxy-9α/β,15α/β-dihydroxy-16-(1-chloro-2-naphthyloxy)-17,20-tetranor-5-cis,13-trans-prostadienoic acid |
| 307 | Example 164 | dl-11-deoxy-9α/β,15α-dihydroxy-16-(5,6,7,8-tetranor-2-naphthyloxy)-17,20-tetranor-5-cis,13-trans-prostadienoic acid |
| 308 | Example 165 | dl-11-deoxy-9α/β,15β-dihydroxy-16-benzyloxy)-17,20-tetranor-5-cis,13-trans-prostadienoic acid |
| 309 | Example 166 | dl-11-deoxy-9α/β,15β-dihydroxy-16-(2-naphthyloxy-17,20-tetranor-5-cis,13-trans-prostadienoic acid |
| 310 | Example 167 | dl-11-deoxy-9α/β,15β-dihydroxy-16-p-chlorophenoxy-17,20-tetranor-5-cis,13-trans-prostadienoic acid |
| 311 | Example 168 | dl-11-deoxy-9α/β,15β-dihydroxy-16-m-chlorophenoxy-17,20-tetranor-5-cis,13-trans-prostadienoic acid |
| 312 | Example 169 | dl-11-deoxy-9α/β,15β-dihydroxy-16-o-chlorophenoxy-17,20-tetranor-5-cis,13-trans-prostadienoic acid |
| 313 | Example 170 | dl-11-deoxy-9α/β,15β-dihydroxy-16-(2,4-dichlorophenoxy)-17,20-tetranor-5-cis,13-trans-prostadienoic acid |
| 314 | Example 171 | dl-11-deoxy-9α/β,15β-dihydroxy-16-p-fluorophenoxy-17,20-tetranor-5-cis,13-trans-prostadienoic acid |
| 315 | Example 172 | dl-11-deoxy-9α/β,15β-dihydroxy-16-m-methylphenoxy-17,20-tetranor-5-cis,13-trans-prostadienoic acid |
| 316 | Example 173 | dl-11-deoxy-9α/β,15β-dihydroxy-16-p-trifluoromethyl-phenoxy-17,20-tetranor-5-cis,13-trans-prostadienoic acid |
| 317 | Example 174 | dl-11-deoxy-9α/β,15β-dihydroxy-16-p-methoxyphenoxy-17,20-tetranor-5-cis,13-trans-prostadienoic acid |
| 318 | Example 175 | dl-11-deoxy-9α/β,15β-dihydroxy-16-o-methoxyphenoxy-17,20-tetranor-5-cis,13-trans-prostadienoic acid |
| 319 | Example 176 | dl-11-deoxy-9α/β,15β-dihydroxy-16-m-fluorophenoxy-17,20-tetranor-5-cis,13-trans-prostadienoic acid |
| 320 | Example 177 | dl-11-deoxy-9α/β,15β-dihydroxy-16-o-fluorophenoxy-17,20-tetranor-5-cis,13-trans-prostadienoic acid |
| 321 | Example 178 | dl-11-deoxy-9α/β,15β-dihydroxy-16-o-methylphenoxy-17,20-tetranor-5-cis,13-trans-prostadienoic acid |
| 322 | Example 179 | dl-11-deoxy-9α/β,15β-dihydroxy-16-m-dimethylamino-phenoxy-17,20-tetranor-5-cis,13-trans-prostadienoic acid |
| 323 | Example 180 | dl-11-deoxy-9α/β,15β-dihydroxy-16-(1-naphthyloxy)-17,20-tetranor-5-cis,13-trans-prostadienoic acid |
| 324 | Example 181 | dl-11-deoxy-9α/β,15β-dihydroxy-16-(6-methoxy-2-naphthyl-oxy)-17,20-tetranor-5-cis,13-trans-prosadienoic acid |
| 325 | Example 182 | dl-11-deoxy-9α/β,15β-dihydroxy-16-(2,3-dichlorophenoxy)-17,20-tetranor-5-cis,13-trans-prostadienoic acid |

TABLE 7-continued

| Example | 9-Oxo Compound | Product 9,15-Diols |
|---|---|---|
| 326 | Example 183 | dl-11-deoxy-9α/β,15β-dihydroxy-16-(3,5-dichlorophenoxy)-17,20-tetranor-5-cis,13-trans-prostadienoic acid |
| 327 | Example 184 | dl-11-deoxy-9α/β,15β-dihydroxy-16-m-methoxyphenoxy-17,20-tetranor-5-cis,13-trans-prostadienoic acid |
| 328 | Example 185 | dl-11-deoxy-9α/β,15β-dihydroxy-16-(5,6,7,8-tetrahydro-2-naphthyloxy-17,20-tetranor-5-cis,13-trans-prostadienoic acid |
| 329 | Example 186 | dl-11-deoxy-9α/β,15β-dihydroxy-16-phenoxy-17,20-tetranor-5-cis,13-trans-prostadienoic acid |
| 330 | Example 187 | dl-11-deoxy-15α-hydroxy-9-oxo-16-phenoxy-17,20-tetranor-13-trans-prostenoic acid |
| 331 | Example 188 | dl-11-deoxy-9α/β,15α/β-dihydroxy-16-p-methylphenoxy-17,20-tetranor-13-trans-prostenoic acid |
| 332 | Example 189 | dl-11-deoxy-9α/β,15α-dihydroxy-16-m-methylphenoxy-17,20-tetranor-13-trans-prostenoic acid |
| 333 | Example 190 | dl-11-deoxy-9α/β,15α-dihydroxy-16-(3,5-dimethylphenoxy)-17,20-tetranor-13-trans-prostenoic acid |
| 334 | Example 191 | dl-11-deoxy-9α/β,15β-dihydroxy-16-o-methoxyphenoxy-17,20-tetranor-13-trans-prostenoic acid |
| 335 | Example 192 | dl-11-deoxy-9α/β,15α-dihydroxy-16-o-methylphenoxy-17,20-tetranor-13-trans-prostenoic acid |
| 336 | Example 193 | dl-11-deoxy-9α/β,15β-dihydroxy-16-p-methoxyphenoxy-17,20-tetranor-13-trans-prostenoic acid |
| 337 | Example 194 | dl-11-deoxy-9α/β,15β-dihydroxy-16-m-dimethylaminophenoxy-17,20-tetranor-13-trans-prostenoic acid |
| 338 | Example 195 | dl-11-deoxy-9α/β,15α-dihydroxy-16-phenoxy-17,20-tetranor-prostanoic acid |
| 339 | Example 196 | dl-11-deoxy-9α/β,15α/β-dihydroxy-16-p-methylphenoxy-17,20-tetranor-prostanoic acid |
| 340 | Example 197 | dl-11-deoxy-9α/β,15α-dihydroxy-16-m-methylphenoxy-17,20-tetranor-prostanoic acid |
| 341 | Example 198 | dl-11-deoxy-9α/β,15α-dihydroxy-16-(3,5-dimethylphenoxy)-17,20-tetranor-prostanoic acid |
| 342 | Example 199 | dl-11-deoxy-9α/β,15β-dihydroxy-16-o-methoxyphenoxy-17,20-tetranor-prostanoic acid |
| 343 | Example 200 | dl-11-deoxy-9α/β,15α-dihydroxy-16-o-methylphenoxy-17,20-tetranor-prostanoic acid |
| 344 | Example 201 | dl-11-deoxy-9α/β,15β-dihydroxy-16-p-methoxyphenoxy-17,20-tetranor-prostanoic acid |
| 345 | Example 202 | dl-11-deoxy-9α/β,15β-dihydroxy-16-m-dimethylaminophenoxy-17,20-tetranor-prostanoic acid |

EXAMPLE 346

Preparation of dl-11-deoxy-15α-hydroxy-9-oxo-16-phenoxy-17,20-tetranor-5-cis,13-trans-prostadienoic acid methyl ester 150 mg. of dl-11-deoxy-15α-hydroxy-9-oxo-16-phenoxy-17,20-tetranor-5-cis,13-trans-prostadienoic acid is dissolved in 10 ml. of ether, cooled to 0° C. and an ethereal diazomethane solution is added until a persistant yellow color is observed. The excess diazomethane and solvent is removed under a stream of argon to provide the subject compound: λmax. 3400, 1740, 975 cm$^{-1}$.

EXAMPLES 347–356

The compounds of the following table when esterified with the appropriate diazoalkane by the procedure of Example 346 provide the product prostaglandin esters of the following table.

TABLE 8

| Example | Starting Acid | Diazoalkane | Product Prostaglandin Ester |
|---|---|---|---|
| 347 | Example 131 | diazoethane | dl-11-deoxy-15α-hydroxy-9-oxo-16-benzyloxy-17,20-tetranor-5-cis,13-trans-prostadienoic acid ethyl ester |
| 348 | Example 134 | diazopropane | dl-11-deoxy-15α-hydroxy-9-oxo-16-m-chlorophenoxy-17,20-tetranor-5-cis,13-trans-prostadienoic acid propyl ester |
| 349 | Example 138 | diazobutane | dl-11-deoxy-15α-hydroxy-9-oxo-16-p-fluorophenoxy-17,20-tetranor-5-cis,13-trans-prostadienoic acid butyl ester |
| 350 | Example 142 | diazopentane | dl-11-deoxy-15α-hydroxy-9-oxo-16-p-trifluoromethylphenoxy-17,20-tetranor-5-cis,13-trans-prostadienoic acid pentyl ester |
| 351 | Example 163 | diazohexane | dl-11-deoxy-15α/β-hydroxy-9-oxo-16-(1-chloro-2-naphthyloxy)-17,20-tetranor-5-cis,13-trans-prostadienoic acid hexyl ester |
| 352 | Example 172 | diasoheptane | dl-11-deoxy-15β-hydroxy-9-oxo-16-m-methylphenoxy-17,20-tetranor-5-cis,13-trans-prostadienoic acid heptyl ester |
| 353 | Example 188 | diazooctane | dl-11-deoxy-15α/β-hydroxy-9-oxo-16-p-methylphenoxy-17,20-tetranor-13-trans-prostenoic acid octyl ester |
| 354 | Example 202 | diazononane | dl-11-deoxy-9-oxo-15α-hydroxy-16-m-dimethyl- |

TABLE 8-continued

| Example | Starting Acid | Diazoalkane | Product Prostaglandin Ester |
|---|---|---|---|
| | | | aminophenoxy-17,20-tetranor-prostanoic acid nonyl ester |
| 355 | Example 207 | diazodecane | dl-11-deoxy-9α,15α-dihydroxy-16-m-chloro-phenoxy-17,20-tetranor-5-cis,13-trans-prostadienoic acid decyl ester |
| 356 | Example 316 | diazomethane | dl-11-deoxy-9β-15β-dihydroxy-16-p-trifluoromethylphenoxy-17,20-tetranor-5-cis,13-trans-prostadienoic acid methyl ester |

We claim:

1. A compound selected from the group consisting of an optically active compound of the formula:

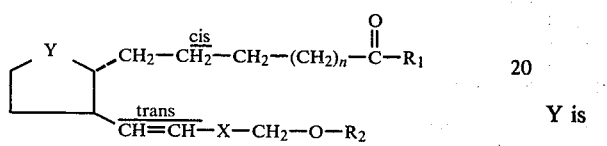

and a racemic compound of that formula and the mirror image thereof; wherein $R_1$ is hydroxy or alkoxy having from 1 to 12 carbon atoms; $R_2$ is a phenyl, benzyl, naphthyl, or 5,6,7,8-tetrahydronaphthyl group optionally substituted with one or two members selected from the group consisting of halogen, lower alkyl, lower alkoxy and trifluoromethyl; n is an integer from 2 to 4, inclusive; X is a divalent moiety selected from the group consisting of those of the formulae:

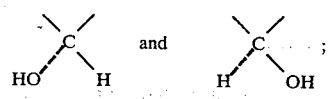

Y is a divalent moiety selected from the group consisting of those of the formulae:

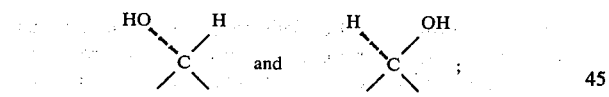

and the non-toxic cationic salts thereof when $R_1$ is hydroxy.

2. The enantiomer according to claim 1 wherein X is

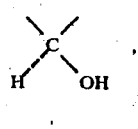

Y is

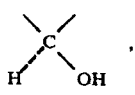

$R_1$ is hydroxy, $R_2$ is o-fluorophenyl, and n is three; 1-9α,15α-dihydroxy-16-o-fluorophenoxy-17,20-tetranor-13-trans-prostenoic acid.

3. The racemate according to claim 1 wherein X is

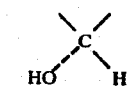

Y is

$R_1$ is hydroxy, $R_2$ is o-fluorophenyl, and n is three; dl-9α,15α-dihydroxy-16-o-fluorophenoxy-17,20-tetranor-13-trans-prostenoic acid.

4. The enantiomer according to claim 1 wherein X is

Y is

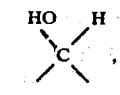

$R_1$ is hydroxy, $R_2$ is p-fluorophenyl, and n is three, 1-9α,15β-dihydroxy-16-p-fluorophenoxy-17,20-tetranor-13-trans prostenoic acid.

5. The racemate according to claim 1 wherein X is

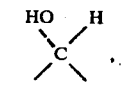

Y is

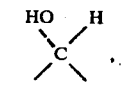

$R_1$ is hydroxy, $R_2$ is p-fluorophenyl, and n is three, dl-9α,15β-dihydroxy-16-p-fluorophenoxy-17,20-tetranor-13-trans-prostenoic acid.

6. The enantiomer according to claim 1 wherein X is

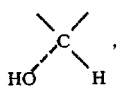

Y is

$R_1$ is hydroxy, $R_2$ is p-chlorophenyl, and n is three; l-9α,15α-dihydroxy-16-p-chlorophenoxy-17,20-tetranor-13-trans-prostenoic acid.

7. The racemate according to claim 1 wherein X is

Y is

$R_1$ is hydroxy, $R_2$ is p-chlorophenyl, and n is three; dl-9α,15α-dihydroxy-16-p-chlorophenoxy-17,20-tetranor-13-trans-prostenoic acid.

8. The enantiomer according to claim 1 wherein X is

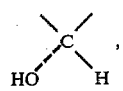

Y is

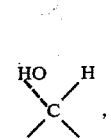

$R_1$ is hydroxy, $R_2$ is m-trifluoromethylphenyl, and n is three; l-9α,15α-dihydroxy-16-m-trifluoromethylphenoxy-17,20-tetranor-13-trans-prostenoic acid.

9. The recemate according to claim 1 wherein X is

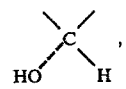

Y is

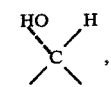

$R_1$ is hydroxy, $R_2$ is m-trifluoromethylphenyl, and n is three; dl-9α,15α-dihydroxy-16-m-trifluoromethylphenoxy-17,20-tetranor-13-trans-prostenoic acid.

* * * * *